(12) United States Patent
Williams et al.

(10) Patent No.: US 9,884,836 B2
(45) Date of Patent: Feb. 6, 2018

(54) 2-SUBSTITUTED-5-HYDROXY-4H-CHROMEN-4-ONES AS NOVEL LIGANDS FOR THE SEROTONIN RECEPTOR 2B (5-HT2B)

(71) Applicant: VIRGINIA COMMONWEALTH UNIVERSITY, Richmond, VA (US)

(72) Inventors: Dwight A. Williams, Richmond, VA (US); Yan Zhang, Glen Allen, VA (US)

(73) Assignee: Virginia Commonwealth University, Richmond, VA (US)

(*) Notice: Subject to any disclaimer, the term of this patent is extended or adjusted under 35 U.S.C. 154(b) by 0 days.

(21) Appl. No.: 15/113,449

(22) PCT Filed: Jan. 22, 2015

(86) PCT No.: PCT/US2015/012355
§ 371 (c)(1),
(2) Date: Jul. 22, 2016

(87) PCT Pub. No.: WO2015/116460
PCT Pub. Date: Aug. 6, 2015

(65) Prior Publication Data
US 2017/0029399 A1  Feb. 2, 2017

Related U.S. Application Data

(60) Provisional application No. 61/932,372, filed on Jan. 28, 2014.

(51) Int. Cl.
*C07D 311/22* (2006.01)
*C07D 407/06* (2006.01)
*C07D 409/06* (2006.01)

(52) U.S. Cl.
CPC .......... *C07D 311/22* (2013.01); *C07D 407/06* (2013.01); *C07D 409/06* (2013.01)

(58) Field of Classification Search
CPC ... C07D 311/22; C07D 407/06; C07D 409/06
See application file for complete search history.

(56) References Cited

FOREIGN PATENT DOCUMENTS

| EP | 2386546 A1 | | 11/2011 |
|---|---|---|---|
| JP | 2008156297 | * | 7/2010 |
| WO | 2004/037193 A2 | | 5/2004 |
| WO | 2005/016338 A1 | | 2/2005 |

OTHER PUBLICATIONS

Williams et al. Tetrahedron Letters 54 (2013) 4292-4295.*
Williams et al Tetrahedron Letters 54 (2013) 4292-4295.*
Williams et al., "An efficient procedure for the preparation of natural products bearing the 2-(2-phenylethyl)chromone skeleton", Tetrahedron Letters, 2005, pp. 4292-4295, vol. 54.
Legoabe et al., "Selected chromone derivatives as inhibitors of monamine oxidase", Bioorg. Med. Chem. Lett., 2012, pp. 5480-5484, vol. 22.

* cited by examiner

*Primary Examiner* — Shirley V Gembeh
(74) *Attorney, Agent, or Firm* — Whitham, Curtis & Cook, P.C.

(57) ABSTRACT

A family of compounds which function as selective ligands for the serotonin receptor 2B (5-HT$_{2B}$) is identified. Some of the compounds are synthetic non-natural ligands which have a relatively strong interaction with 5-HT2B compared to naturally occurring compounds (some of which are identified for the first time herein as ligands for 5-HT$_{2B}$). Because the compounds, both naturally occurring and synthetically produced, function as ligands for 5-HT$_{2B}$ they will have application in, for example, the treatment and/or prevention of nervous system disorders such as Alzheimer's disease.

3 Claims, 16 Drawing Sheets

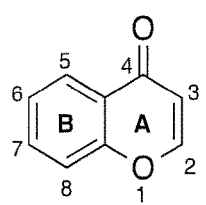
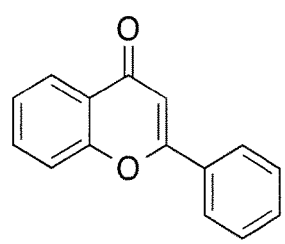
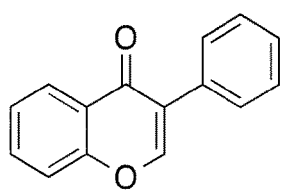
      6                     7                   8
Chromone        Flavone       Isoflavone
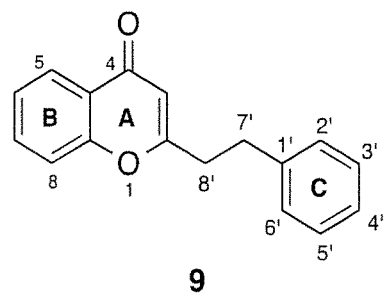
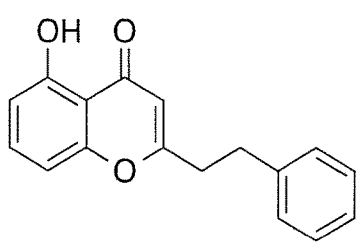
        9                         10
2-(2-phenylethyl)chromone    5-Hydroxy-2-(2-phenylethyl)chromone
                                               (5-HPEC)
Figure 2

27 →ⁱⁱ→ Complex Mixture

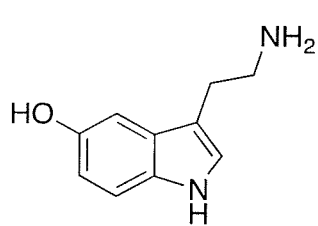
Serotonin (34)
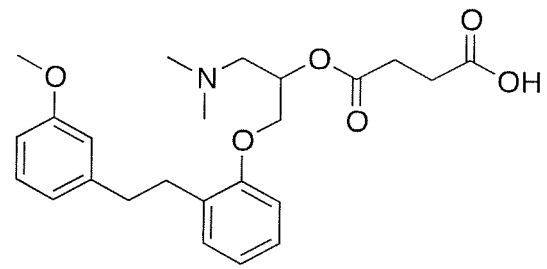
Sarbogrelate (35)
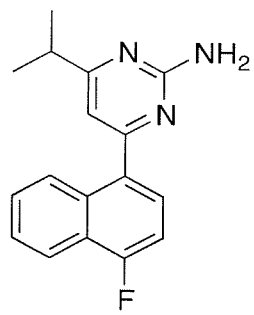
RS 127445 (4)
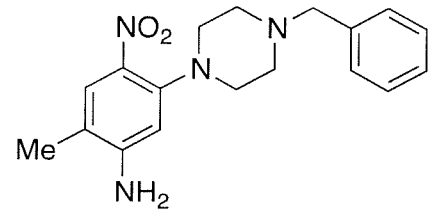
EGIS-7625 (2)
Figure 10

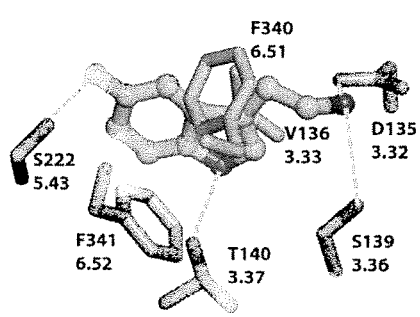 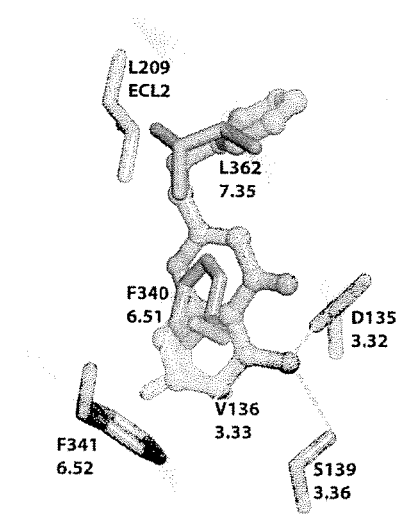
Figure 11A                    Figure 11B 22a, 22e, 22g, 22h, 22i, and 22r

2-SUBSTITUTED-5-HYDROXY-4H-CHROMEN-4-ONES AS NOVEL LIGANDS FOR THE SEROTONIN RECEPTOR 2B (5-HT2B)

BACKGROUND OF THE INVENTION

Field of the Invention

Embodiments of the invention generally relate to compounds that are useful as selective ligands for the serotonin receptor 2B (5-HT$_{2B}$). Some of the compounds are synthetic non-natural ligands which have a relatively strong interaction with 5-HT$_{2B}$ compared to naturally occurring compounds (some of which are identified for the first time herein as ligands for 5-HT$_{2B}$). Because the compounds, both naturally occurring and synthetically produced, function as ligands for 5-HT$_{2B}$ they will have application in, for example, the treatment and/or prevention of nervous system disorders such as Alzheimer's disease.

Background of the Invention

Serotonin (or 5-hydroxytryptamine, 5-HT) is a well-known neurotransmitter of the peripheral and central nervous systems (PNS and CNS).[1, 2] 5-HT is often associated with mood disorders such as depression and schizophrenia; however the role of 5-HT extends beyond controlling mood. Specifically, 5-HT has been shown to be involved in controlling food intake, gastrointestinal function, cardiovascular function, cell development, drug seeking behavior, and pain.[2, 3] The numerous functions of 5-HT can be attributed to the diversity in its receptors.[4] Presently there are seven 5-HT receptor families (designated 5-HT$_{1-7}$) with each having their own unique pharmacology. Thus, there is a need for small molecules to selectively target 5-HT receptor subtypes to treat a wide variety of conditions and/or diseases associated with 5-HT signaling.

The Serotonin receptor 2 (5-HT$_2$) subfamily consists of three subtypes: 5-HT$_{2A}$, 5-HT$_{2B}$ and 5-HT$_{2C}$.[5] The 5-HT$_{2B}$ receptor was initially identified in isolated preparations of the rat fundus and was found to regulate contractions.[6] In humans, 5-HT$_{2B}$ can be found in both the peripheral and central nervous system.[5] The 5-HT$_{2B}$ receptor binds the neurotransmitter serotonin and mediates many of the central and peripheral physiologic functions of serotonin. 5-HT$_{2B}$ receptors regulate serotonin release via the serotonin transporter, and are important both to normal physiological regulation of serotonin levels in blood plasma, and with the abnormal acute serotonin release produced by drugs such as MDMA. Some effects of serotonin on the CNS include presynaptic inhibition, neuronal sensitization to tactile stimuli, mediation of some of the effects of hallucinogenic substituted amphetamines, and behavioral modifications.

Recently there has been a resurgence in developing selective antagonists for 5-HT$_{2B}$ for the treatment of irritable bowel syndrome, migraine, pulmonary hypertension, and drug abuse.[7] There is also evidence that antagonists of 5-HT$_{2B}$ may also be suitable neuroprotectants useful for treating neurodegenerative diseases.[8] Despite the potential use for 5-HT$_{2B}$ antagonists, much work still needs to be done. A notable challenge in developing ligands for 5-HT$_{2B}$ is that of selectivity.[9] 5-HT$_{2B}$ shares approximately 46-50% sequence identity with 5-HT$_{2A/C}$ and their homology within the transmembrane domain (which contains the 5-HT binding pocket) is higher than 70%.[5] Thus, the design of selective ligands targeting 5-HT$_{2B}$ over 5-HT$_{2A/C}$ is a challenge. Currently, there are a limited number of ligands selective for 5-HT$_{2B}$ Among the available ligands, some of the more commonly used structural scaffolds are: arylureas (1), arylpiperazines (2), indolonapthyridines (3), pyrimidines (4), and therahydro-β-carbolynes (5) (FIG. 1).[7]

The role of natural products in helping to understand the biochemical bases of human diseases is well established.[12] One class of natural products with a long history of having beneficial biological effects are chromones (6) (FIG. 2).[13] Chromones are heterocyclic compounds readily identified by their benzoannelated γ-pyrone core and have been isolated from both terrestrial and marine sources.[13] Compounds containing the chromone core have shown a broad range of activities, which include but are not limited to antioxidants[14], anti-inflammatory[15], antivirals[16], and neuroprotectants[17, 18]. Within the chromone superfamily smaller subfamilies exist and are identified most often by the position and nature of the substituent on the "A" ring. Examples of these subfamilies are flavones (7), isoflavones (8) and 2-(2-phenylethyl)chromones (9) (FIG. 2). Among these, the 2-(2-phenethyl)chromones (9) are the least understood.

Neurodegenerative diseases affecting the central nervous system (CNS) are widely spread among the population.[20] Consequently, tremendous research effort has been directed towards the development and application of small molecules to study the proteins involved in these CNS disorders.[21] Thus far, most of the research on the therapeutic value of chromones as related to CNS disorders has been correlated only to their antioxidant properties.[14] Until recently, little attention has been paid to the ability of chromones to serve as small molecule modulators of enzymes and receptors within the CNS.[23-25] Lately, 2-(2-phenylethyl)chromones (9), a relatively small and under-explored class of chromones have shown promise as potential tools to study CNS related disorders.[26] Unlike the flavonoids, these chromones possess a phenylethyl substituent at C2 and to date less than 100 congeners of 2-(2-phenylethyl)chromone have been isolated and characterized.[19] Yoon et. al. isolated 5-hydroxy-2-(2-phenylethyl)chromone (5-HPEC, 10) from *Imperata cylindrical* and showed that this compound had neuroprotective activity against glutamate induced excitotoxicity in primary cultures of rat cortical cells.[17] The neurotoxic effects of glutamate have been shown to involve not only glutamate receptors but also non-glutamate receptors, ion channels, and transporters.[27,28] Thus, elucidation of the potential molecular target(s) of 5-HPEC would be necessary in order to further study the role of this type of compound in their CNS neuroprotection mechanism and to develop potential therapeutics.

SUMMARY OF THE INVENTION

Embodiments of the invention include a class of compounds that are selective inhibitors for the 5-HT$_{2B}$ receptor. The presence of a basic nitrogen atom was previously thought to be required for ligand binding of the 5-HT$_{2B}$ receptor and pharmacological action.[10] The invention is based on the surprising discovery that certain non-nitrogenous compounds are selective antagonists of the 5-HT$_{2B}$ receptor. The compounds have a skeleton derived from 5-HPEC, a naturally-occurring non-nitrogenous antagonist. It has been discovered that 5-HPEC is a 5-HT$_{2B}$ receptor antagonist. Hence, in an embodiment of the invention, a new class of 2-substituted-5-hydroxy-4H-chromen-4-one compounds are identified that are selective non-nitrogenous antagonists of the 5-HT$_{2B}$ receptor.

Another embodiment of the invention includes modified analogues of 5-HPEC which have enhanced selectivity for and activity at the 5-HT$_{2B}$ receptor. These include synthesized non-natural analogues that are optimized to enhance selectivity for and activity at the 5-HT$_{2B}$ receptor.

Another embodiment of the invention includes a composition comprising one or more compounds that are selective non-nitrogenous analogues of 5-HT$_{2B}$ together with a pharmaceutically acceptable solid, liquid or aqueous carrier.

Another embodiment of the invention includes the use of one or more compounds that are selective non-nitrogenous analogues of 5-HT$_{2B}$ in the treatment or prevention of diseases and disorders of the central nervous system (CNS), including but not limited to Alzheimer's disease, Parkinson's disease, amyotrophic lateral sclerosis, stroke, traumatic brain injury, and drug abuse and addiction, and diseases and disorders associated with the PNS, such as irritable bowel syndrome and pulmonary hypertension.

Another embodiment is a method of preventing, treating, or slowing the progression of symptoms of a nervous system disorder in a patient (human or animal) in need thereof, comprising the step of administering a therapeutically effective amount of at least one compound which is a newly discovered selective non-nitrogenous analogs of 5-HT$_{2B}$.

A further embodiment of the invention is a method of inhibiting the 5-HT$_{2B}$ receptor, comprising the step of administering a therapeutically effective amount of at least one compound of the invention. Another embodiment of the invention is a method for treatment of CNS disorders, comprising the step of administering a therapeutically effective amount of at least one compound of the invention that acts through antagonism of 5-HT$_{2B}$ receptor to disrupt serotonergic mechanisms, protect neurons against excitotoxicity, and reduce neurodegeneration.

BRIEF DESCRIPTION OF THE DRAWINGS

FIG. 2. Chromone Core (6), flavone (7), isoflavone (8), 2-(2-phenylethyl)chromone (9) and 5-hydroxy-2-(2-phenylethyl)chromone (10) with numbering.

FIG. 10: The chemical structures of serotonin and selected 5-HT$_{2B}$ antagonists.

FIG. 11A-B: a) Docking of serotonin (5-HT) in the 5-HT$_{2B}$ receptor. b) Putative binding mode of 5-HPEC (10) in the 5-HT$_{2B}$ receptor. Small molecules are shown in balls and sticks and residues in sticks. Numbers "x.yy" refer to Ballesteros-Weinstein numbering. Possible hydrogen bonds are shown with dashed lines.

DETAILED DESCRIPTION

Figure 1:
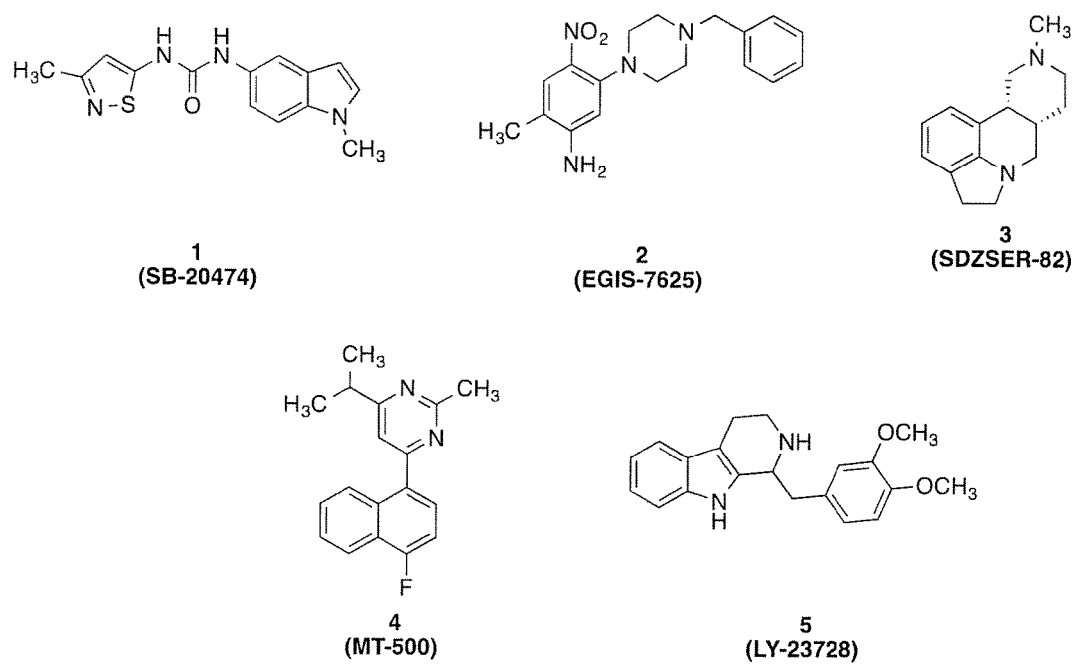
FIG. 1. Structural scaffolds of known 5-HT$_{2B}$ antagonists: arylureas (1), arylpiperazines (2), indolonapthyridines (3), pyrimidines(4), and therahydro-β-carbolynes (5).

Embodiments of the invention include novel compounds that selectively bind and antagonize the 5-HT$_{2B}$ receptor. Some of the compounds of the invention are 5-HPEC analogues produced by de novo synthesis (e.g. synthesized non-naturally occurring compounds). Other compounds include naturally-occurring molecules that selectively bind and antagonize the 5-HT$_{2B}$ receptor. In an embodiment of the invention, a new class of 2-substituted-5-hydroxy-4H-chromen-4-one compounds are identified that are selective non-nitrogenous antagonists of the 5-HT$_{2B}$ receptor. Another embodiment of the invention includes modified analogues of 5-HPEC which have enhanced selectivity for and activity at the 5-HT$_{2B}$ receptor. These include synthesized non-natural analogues that are optimized to enhance selectivity for and activity at the 5-HT$_{2B}$ receptor.

These molecules constitute new compositions of matter and can be combined with other constituents and carriers (solid and liquid) to produce compositions that can be formulated as pharmaceuticals for inhibition of the 5-HT$_{2B}$ receptor and for the treatment of diseases and disorders of the CNS, including but not limited to Alzheimer's disease, Parkinson's disease, amyotrophic lateral sclerosis, stroke, traumatic brain injury, and drug abuse and addiction, and diseases and disorders associated with the PNS, such as irritable bowel syndrome and pulmonary hypertension.

Embodiments of the invention provide compounds having the general formula:

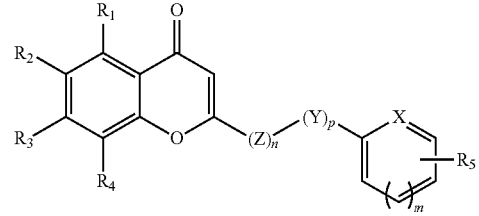

wherein
R1, R2, R3, and R4 can be the same or different and are selected from the group consisting of H, OH, SH, sulfanyl, amino, alkyl, alkoxyl, halogen, alkenyl, alkynyl, aryl, cyano, nitro, carboxyl, carbonyl, sulfone, and sulfoxide;
R5 is either present or absent and if present is selected from the group consisting of OH, SH, sulfanyl, amino, alkyl, alkoxyl, halogen, alkenyl, alkynyl, aryl, cyano, nitro, carboxyl, carbonyl, sulfone, sulfoxide, and a substituted or unsubstituted aromatic or heteroaromatic group connected to any two carbon moieties of the ring structure;

X is S, O, or substituted or unsubstituted $C_1$ alkyl; and

Z and Y can be the same or different and can be present or absent and when present are selected from the group consisting of O and a substituted or unsubstituted $C_1$-$C_4$ alkyl, wherein m, n, and p can be the same or different and are selected from the group consisting of 0, 1, 2, and 3; or salts or solvates thereof.

In some embodiments, the compound has the general formula:

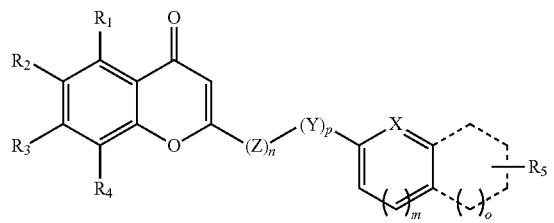

wherein

R1, R2, R3, and R4 can be the same or different and are selected from the group consisting of H, OH, SH, sulfanyl, amino, alkyl, alkoxyl, halogen, alkenyl, alkynyl, aryl, cyano, nitro, carboxyl, carbonyl, sulfone, and sulfoxide;

R5 is either present or absent and if present is selected from the group consisting of OH, SH, sulfanyl, amino, alkyl, alkoxyl, halogen, alkenyl, alkynyl, aryl, cyano, nitro, carboxyl, carbonyl, sulfone, sulfoxide, and a substituted or unsubstituted aromatic or heteroaromatic group connected to any two carbon moieties of the ring structure; X is S, O, or substituted or unsubstituted $C_1$ alkyl; and Z and Y can be the same or different and can be present or absent and when present are selected from the group consisting of O and a substituted or unsubstituted $C_1$-$C_4$ alkyl, wherein m, n, o, and p can be the same or different and are selected from the group consisting of 0, 1, 2, and 3; or salts or solvates thereof.

The compounds of the invention include natural products, but may also be synthesized non-natural compounds. A natural product is a compound that can be found or isolated from a naturally occurring environment. Natural products that fit the 2-(2-phenylethyl)chromone skeleton are shown in Table 1.

TABLE 1

Natural products fitting the 2-(2-phenylethyl)chromone skeleton.

| STRUCTURE | NAME |
|---|---|
| 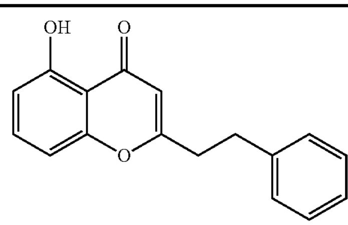 | 5-hydroxy-2-phenethyl-4H-chromen-4-one<br>5-HPEC (10) |
| 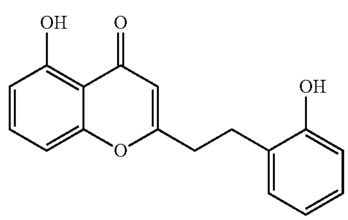 [SMILES: O=c1cc(CCc2ccccc2O)oc2cccc(O)c12] | 5-hydroxy-2-(2-hydroxyphenethyl)-4H-chromen-4-one<br>22b |
| 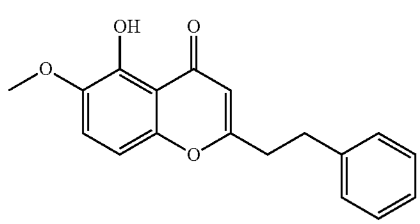 [SMILES: COc1ccc2oc(CCc3ccccc3)cc(=O)c2c1O] | 5-hydroxy-6-methoxy-2-phenethyl-4H-chromen-4-one |
| 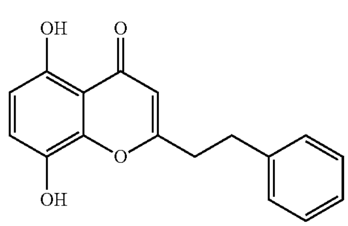 [SMILES: O=c1cc(CCc2ccccc2)oc2c(O)ccc(O)c12] | 5,8-dihydroxy-2-phenethyl-4H-chromen-4-one |

TABLE 1-continued

Natural products fitting the 2-(2-phenylethyl)chromone skeleton.

| STRUCTURE | NAME |
|---|---|
| 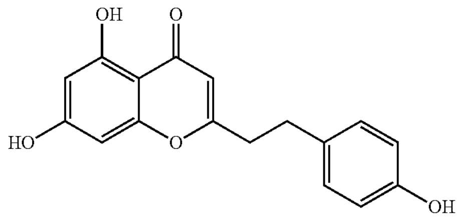 [SMILES: O=c1cc(CCc2ccc(O)cc2)oc2cc(O)cc(O)c12] | 5,7-dihydroxy-2-(4-hydroxyphenethyl)-4H-chromen-4-one |
| 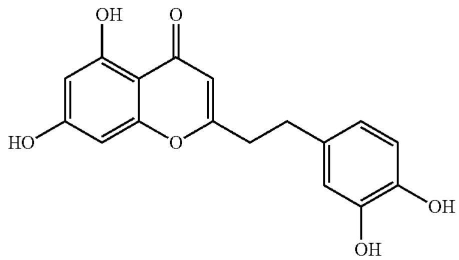 [SMILES: O=c1cc(CCc2ccc(O)c(O)c2)oc2cc(O)cc(O)c12] | 2-(3,4-dihydroxyphenethyl)-5,7-dihydroxy-4H-chromen-4-one |
| 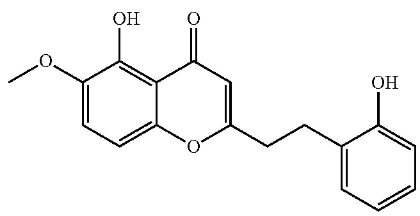 [SMILES: COc1ccc2oc(CCc3ccccc3O)cc(=O)c2c1O] | 5-hydroxy-2-(2-hydroxyphenethyl)-6-methoxy-4H-chromen-4-one |
| 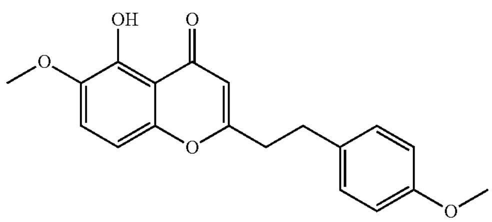 | 5-hydroxy-6-methoxy-2-(4-methoxyphenethyl)-4H-chromen-4-one |
| 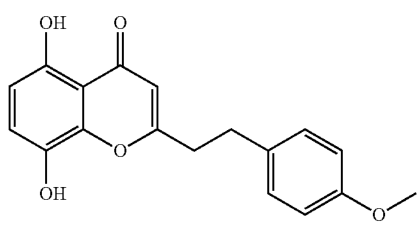 [SMILES: COc1ccc(CCc2cc(=O)c3c(O)ccc(O)c3o2)cc1] | 5,8-dihydroxy-2-(4-methoxyphenethyl)-4H-chromen-4-one |
| 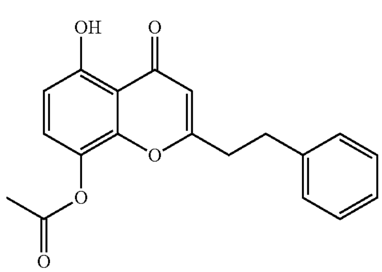 [SMILES: CC(=O)Oc1ccc(O)c2c(=O)cc(CCc3ccccc3)oc12] | 5-hydroxy-4-oxo-2-phenethyl-4H-chromen-8-yl acetate |

TABLE 1-continued

Natural products fitting the 2-(2-phenylethyl)chromone skeleton.

| STRUCTURE | NAME |
|---|---|
| 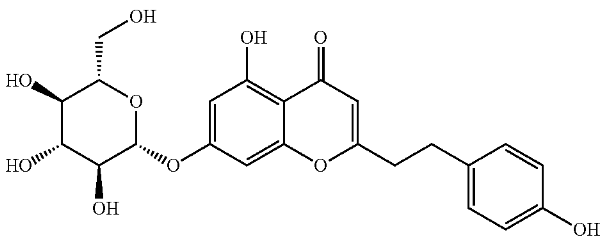 [SMILES: O=c1cc(CCc2ccc(O)cc2)oc2cc(O[C@H]3O[C@@H](CO)[C@H](O)[C@@H](O)[C@@H]3O)cc(O)c12] | 5-hydroxy-2-(4-hydroxyphenethyl)-7-(((2R,3S,4R,5R,6S)-3,4,5-trihydroxy-6-(hydroxymethyl)tetrahydro-2H-pyran-2-yl)oxy)-4H-chromen-4-one |
| 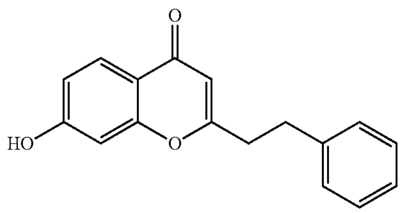 [SMILES: O=c1cc(CCc2ccccc2)oc2cc(O)ccc12] | 7-hydroxy-2-phenethyl-4H-chromen-4-one |
| | 3,7-dihydroxy-2-phenethyl-4H-chromen-4-one<br>7-HPEC (22k) |
| 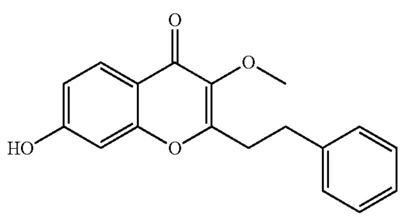 [SMILES: COc1c(CCc2ccccc2)oc2cc(O)ccc2c1=O] | 7-hydroxy-3-methoxy-2-phenethyl-4H-chromen-4-one |
| | 7-hydroxy-2-(4-hydroxyphenethyl)-4H-chromen-4-one<br>22n |
| 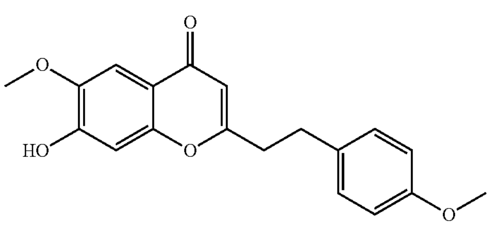 | 7-hydroxy-6-methoxy-2-(4-methoxyphenethyl)-4H-chromen-4-one |
| 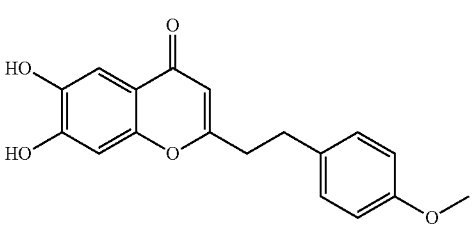 [SMILES: COc1ccc(CCc2cc(=O)c3cc(O)c(O)cc3o2)cc1] | 6,7-dihydroxy-2-(4-methoxyphenethyl)-4H-chromen-4-one |

TABLE 1-continued

Natural products fitting the 2-(2-phenylethyl)chromone skeleton.

| STRUCTURE | NAME |
|---|---|
| 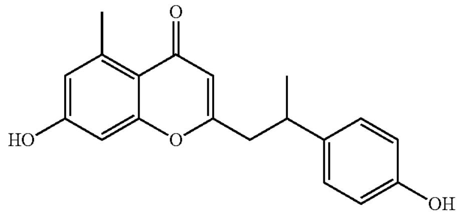 [SMILES: Cc1cc(O)cc2oc(CC(C)c3ccc(O)cc3)cc(=O)c12] | 7-hydroxy-2-(2-(4-hydroxyphenyl)propyl)-5-methyl-4H-chromen-4-one |
| 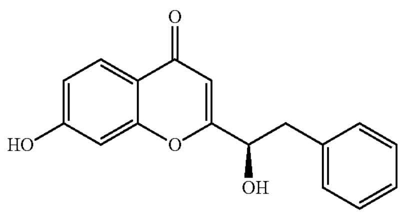 [SMILES: O=c1cc([C@H](O)Cc2ccccc2)oc2cc(O)ccc12] | (R)-7-hydroxy-2-(1-hydroxy-2-phenylethyl)-4H-chromen-4-one |
| 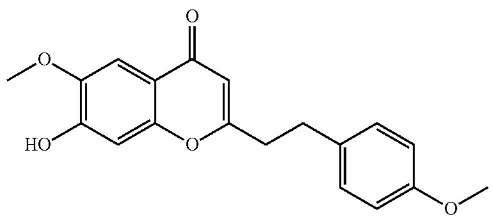 | 7-hydroxy-6-methoxy-2-(4-methoxyphenethyl)-4H-chromen-4-one |
| 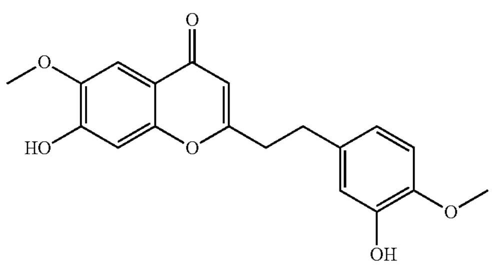 | 7-hydroxy-2-(3-hydroxy-4-methoxyphenethyl)-6-methoxy-4H-chromen-4-one |

A non-natural product is a compound that is artificially produced or synthesized and not found in nature. The term "synthesized" means that the compound is chemically produced (e.g. in a laboratory) as opposed to being isolated from the natural environment if it is naturally occurring.

A substituted aromatic or alkyl group refers to the replacement of at least one hydrogen atom with a non-hydrogen atom or group. A heteroaromatic group refers to the replacement of at least one carbon atom of an aromatic ring with a non carbon atom (e.g. N, O, or S).

A solvate is the result of solvation which is an interaction of a solute (i.e. compound of the invention) with a solvent. Solvation leads to stabilization of the solute species in the solution. A solvate refers to the solvated state, whereby an ion in a solution is surrounded or complexed by solvent molecules. Exemplary solvents include, but are not limited to, propylene glycol; polypropylene glycol; polyethylene glycol (for example, polyethylene glycol 300, polyethylene glycol 400, polyethylene glycol 600, polyethylene glycol 900, polyethylene glycol 540 (all available from Union Carbide) and the like); pharmaceutically acceptable alcohols (for example, ethanol or 2-(2-ethoxyethoxy)ethanol (Transcutol®, Gattefosse, Westwood, N.J. 07675) and the like); polyoxyethylene castor oil derivatives (for example, polyoxyethyleneglycerol triricinoleate or polyoxyl 35 castor oil (CremophorOEL, BASF Corp.), polyoxyethyleneglycerol oxystearate (Cremophor®RH 40 (polyethyleneglycol 40 hydrogenated castor oil) or Cremophor®RH 60 (polyethyleneglycol 60 hydrogenated castor oil), BASF Corp.) and the like); fractionated coconut oil (for example, mixed triglycerides with caprylic acid and capric acid (Miglyol®812, available from Huls AG, Witten, Germany) and the like); Tween®80; isopropyl palmitate; isopropyl myristate; pharmaceutically acceptable silicon fluids; and the like.

"Salts" or "pharmaceutically acceptable salts" refers to the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-.beta.-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," J. Pharm. Sci., 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use such as ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

The Examples provided herein demonstrate that the compounds of the invention bind and inhibit the 5-HT$_{2B}$ receptor, depending on modification of conditions such as dosage, formulation, or route of administration. Compositions comprising at least one of the non-nitrogenous compounds described herein are used for treatment of diseases and disorders of the CNS and PNS. More broadly, CNS disease or disorder affects either the brain or the spinal cord, resulting in neurological or psychiatric disorders such as neurodegenerative diseases, mood disorders, schizophrenia, and autism. Causes of CNS diseases include, but are not limited to, trauma, infections, degeneration, autoimmune disorders, structural defects, tumors, and stroke. PNS diseases or disorders affect neural elements other than the brain and spinal cord and have many causes including, but not limited to, diabetes, genetic predispositions (hereditary causes), exposure to toxic chemicals, alcoholism, malnutrition, inflammation (infectious or autoimmune), injury, nerve compression, and by taking certain medications such as those used to treat cancer and HIV/AIDS. A patient with any of these conditions may also benefit from treatment with compositions comprising the compounds described herein.

The methods of the invention involve inhibiting the serotonin receptor 2B (5-HT$_{2B}$ in a subject comprising administering the subject a therapeutically effective amount of at least one compound on the invention. The methods of the invention also involve identifying subjects or patients who might benefit from receiving therapy for any of these diseases or disorders of the CNS or PNS through administration of a composition comprising at least one of the compounds described herein. Such subjects or patients are generally mammals, and usually humans, although this need not always be the case, since veterinary and research related applications of the technology are also contemplated. Generally a suitable subject or patient is identified by a health care professional or professionals using known tests, measurements, or criteria for either already having symptoms of a nervous system disorder, for example AD, or being at risk of developing symptoms of a nervous system disorder such as AD. A suitable treatment protocol is then developed. The methods may also comprise one or more steps related to monitoring the effects or outcome of administration in order to evaluate the treatment protocol and/or to adjust the protocol as required or in a manner that is likely to provide more benefit, e.g. by increasing or decreasing doses of medication, or by changing the particular type of compound that is administered, or by changing the frequency of dosing or the route of administration, etc. While in some cases the improvement or lessening of symptoms (or the prevention of symptoms) that occurs may be complete, e.g. the functioning of the patient returns to or remains normal (as assessed in comparison to suitable control subjects or standardized values obtained therefrom), this need not always be the case. Those of skill in the art will recognize that even a lower level of improvement in symptoms may be highly beneficial to the patient, as may be the slowing of the progression or symptoms of the disease, even if a complete cure does not result.

The term "therapeutically effective amount" refers to an amount of a compound or composition effective to treat a disease or disorder in a subject. The therapeutically effective amount of the compound or composition may reduce and/or prevent or slow the progression to some extent one or more of the symptoms associated with the disease or disorder.

The methods of the invention involve administering compositions comprising at least one (i.e. one or more) of the compounds disclosed herein to a patient in need thereof. The present invention thus also provides compositions which comprise the compounds as described herein, usually together with a pharmacologically suitable carrier or diluent. In some embodiments, one substantially purified compound is present in a composition; in other embodiments more than one compound is present, each compound being substantially purified prior to being mixed in the composition. The preparation of pharmacologically suitable compositions for use as medicaments is well known to those of skill in the art. Typically, such compositions are prepared either as liquid solutions or suspensions, however solid dry forms such as tablets, pills, powders and the like are also contemplated. The liquid may be an aqueous liquid. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of compound in the formulations may vary. However, in general, the amount in the formulations will be from about 1% to about 99%.

The compound compositions (preparations) of the present invention may be administered by any of the many suitable means which are well known to those of skill in the art, including but not limited to: by injection, inhalation, orally, intravaginally, intranasally, by ingestion of a food or product containing the mimic, topically, as eye drops, via sprays, etc. In exemplary embodiments, the mode of administration is orally or by injection. In addition, the compositions may be administered in conjunction with other treatment modalities such as other agents which are used to treat AD or the conditions which cause AD in the patient, examples of which include but are not limited to the administration of anti-depressants and psychoactive drugs, administration of dopamine and similar agents, administration of e.g. donepezil, galantamine, memantine, tacrine, rivastigamine, etc.

The amount of compound that is administered is generally in the range of from about 1 to about 20 mg/kg, and preferably in the range of from about 5 to about 10 mg/kg, although as one of skill in the art will recognize, the precise amount may vary depending on one or more attributes of the drug recipient, including but not limited to: weight, overall health, gender, age, nationality, genetic history, other conditions being treated, etc.

In some embodiments, the compounds described herein are used prophylactically, e.g. they are administered to persons who have not yet exhibited symptoms of the disease but are deemed to be at risk for developing the disease (e.g. those who are known to have a genetic predisposition for disease development), or simply those who are at risk due to other factors such as aging. The compounds may also be administered to individuals who are thought or deemed to be exhibiting early signs of disease or to be in early stages of disease. The compounds may also be administered to individuals who are known to have and who definitely exhibit symptoms of disease. Administration of the compounds described herein may prevent disease symptoms, may slow the progression of disease, and/or may reverse symptoms. Those of skill in the art will recognize that, while complete remission of disease may be desirable, great benefit may also accrue if partial remission or slowing of disease progress is achieved.

Other embodiments of the invention include the treatment of diseases or disorders associated with neurodegeneration. These methods comprise the step of administering a therapeutically effective amount of at least one of the compounds described herein or a composition thereof to a patient in need thereof to treat or prevent neurodegeneration. Examples of such disease or disorders include but are not limited to Parkinson's disease, Huntington's disease, ALS, and prion disease.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

Figure 3:
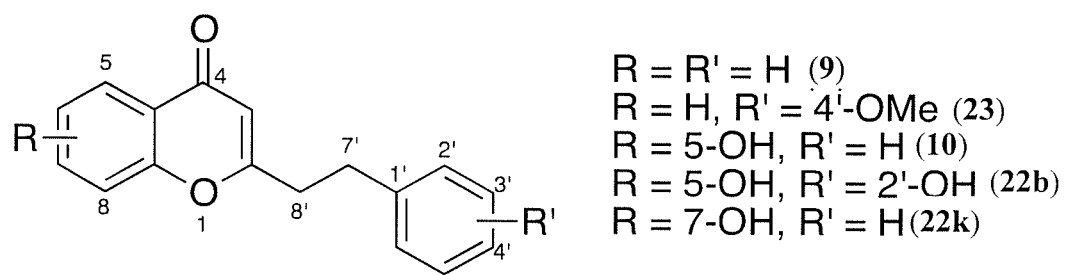
FIG. 3. Several biologically active 2-(2-phenylethyl) chromones.

Example 1. An Efficient Procedure for the Preparation of Products Bearing the 2-(2-Phenylethyl)Chromone Skeleton Introduction Five chromones were previously isolated from *Imperata Cylindrica* and *Aquilaria Malaccensis* (5, 9, 10, 22b, 22k, and 23, FIG. 3).[17,29-30] Unlike flavonoids, these chromones have a phenylethyl substituent at C-2 position, which is quite uncommon.[19] The typical substituent at C-2 for most chromones is an aromatic ring; thus, most literature is targeted towards the synthesis of chromones like 7 (FIG. 2).[31] However, the methods described in the prior art are not useful for the synthesis of chromones bearing the phenylethyl substituent at C-2. The following provides an exemplary method for efficiently and rapidly synthesizing a 2-(2-phenylethyl)chromone skeleton.

Materials and Methods

General Procedures:

Claisen condensation Method A: To a slurry of sodium hydride (4.0 mmol) in refluxing THF was added drop wise the acetophenone 25 (1.0 mmol) dissolved in 10 mL of THF over 10 min. The solution was then allowed to reflux further for 1 h. After cooling to room temperature the ester 26 (1.5 mmol) was added drop wise over 15 min and the resulting solution stirred for 24 h. The reaction mixture was then poured over 50 mL of saturated $NH_4Cl$ and extracted three times with ethyl acetate. The combined organic layers were dried over $Na_2SO_4$ and concentrated to yield the crude product that was used directly without purification for the cyclization step. Method B: A solution of the ester 26 (1.5 mmol) and NaH (4.0 mmol) in THF was brought to reflux while the Acetophenone 25 (1.0 mmol) was added dropwise over 3 min. The resulting solution was refluxed for 4 hours. The reaction mixture was then poured into water and the pH was adjusted to neutral by dropwise addition of 3M HCl. The aqueous layer was extracted three times with dichloromethane ($CH_2Cl_2$). The combined $CH_2Cl_2$ layers were dried over $Na_2SO_4$ and concentrated to yield the crude product that was used directly without purification for the cyclization step. Method C: To a slurry of the corresponding base (3.0 mmol) in THF at 0° C. was added drop wise the acetophenone 25 (1.0 mmol). The resulting solution was allowed to stir at room temperature for 1 h. The ester 26 was then added drop wise and the solution allowed to stir at room temperature for 24 h. The reaction mixture was poured over 50 mL of saturated $NH_4Cl$ and extracted three times with 25 mL of ethyl acetate. The combined organic layers were dried over $Na_2SO_4$ and concentrated. Method D: To a slurry of sodium hydride (4.0 mmol) at reflux in THF was added drop wise over 10 min the acetophenone 25 (1.0 mmol) dissolved in 10 mL of THF. The solution was then allowed to reflux further for 1 h. While still at reflux the ester 26 (1.5 mmol) was then added drop wise over 15 min and the resulting solution stirred at reflux for 4 hours. The reaction mixture was then poured over 50 mL of saturated $NH_4Cl$ and extracted three times with ethyl acetate. The combined organic layers were dried over $Na_2SO_4$ and concentrated to yield the crude product that was used directly without purification for the cyclization step.

Cyclization General Procedure:

Method A: The crude Claisen Condensation produce was dissolved in 20 mL of acetic acid and 15 drops of HCl was then added. The solution was then placed in an oil bath that was preheated to 120° C. The solution began to reflux almost immediately and was refluxed for 45 min. While still hot, the solution was poured onto approximately 20 grams of crushed ice. The aqueous layer was extracted with 25 mL ethyl acetate three times. The combined organic layers were then washed with saturated sodium bicarbonate solution followed by brine. After drying over sodium sulfate the organic layer was concentrated to yield the crude product that was then purified in the appropriate manner. Method B: The crude Claisen Condensation produce was dissolved in 20 mL of methanol and 15 drops of HCl was added. The solution was then placed in an oil bath that was preheated to 90° C. The solution began to reflux almost immediately and was refluxed for 45 min. After cooling to room temperature the solution was made neutral by the drop wise addition of saturated $Na_2CO_3$. The resulting solution was then diluted with 75 mL of dichloromethane. The organic layer was washed once with 25 mL of sat. $NH_4Cl$, dried over $Na_2SO_4$, filtered and concentrated. The cyclized product was then purified in an appropriate manner.

2-phenethyl-4H-chromen-4-one (9) Purified by column chromatography eluting with 70/30 hexanes/ethyl acetate. IR $cm^{-1}$ 3075, 2923, 1642, 1600, 1499, 1463, 1379; $^1$H-NMR (400 MHz, $CD_3CN$): δ, 8.04-8.02 (1H, dd, J=1.6 and 7.8 Hz), 7.71-7.69 (1H, dt J=1.6 and 6.96 Hz), 7.47 (1H, d, J=8.4), 7.41-7.37 (1H, dt, J=0.92 and 7.0 Hz), 7.29-7.12 (5H, m) 6.04 (1H, s), 3.05 (2H, t, J=7.9 Hz), 2.92 (2H, t, J=8.0 Hz); $^{13}$C-NMR (100 MHz, $CD_3CN$) δ 178.4, 169.9, 157.4, 141.4, 134.7, 129.5, 129.4, 127.3, 126.0, 126.0, 124.6, 119.0, 110.7, 36.5, 33.4.

2-(4-methoxyphenethyl)-4H-chromen-4-one (23) Purified by column chromatography eluting with 70/30 hexanes/ethyl acetate. IR $cm^{-1}$ 2930, 28.34 1648, 1609, 1511, 1463, 1243, 846, 821; $^1$H-NMR (400 MHz, $CD_3CN$): δ 8.03 (1H, dd, J=1.52 and 7.96 Hz), 7.69-7.64 (1H, dt J=1.56 and 8.48), 7.44 (1H, d, J=8.36 Hz), 7.37 (1H, t, J=7.76 Hz) 7.13 (2H, d, J=8.56), 6.82 (2H, d, J=8.6 Hz), 6.03 (1H, s) 3.71 (3H, s), 2.95 (2H, t, J=7.0 Hz), 2.85 (2H, t, J=7.72 Hz); $^{13}$C-NMR (100 MHz, $CD_3CN$) δ 178.4, 170.0, 159.2, 157.4, 134.7, 133.2, 130.4, 126.0, 124.6, 119.0, 114.8, 110.7, 55.8, 36.7, 32.5.

5-hydroxy-2-phenethyl-4H-chromen-4-one (10) Purified by column chromatography by gradient elution from 50/50 dichloromethane/hexane to 100% dichloromethane. IR $cm^{-1}$ 2934, 1653, 1616, 1480, 1409, 1258, 845, 802; $^1$H-NMR (400 MHz, $CDCl_3$): δ 12.51 (1H, s, 5-OH), 7.44 (1H, t, J=8.32 Hz), 7.18-7.32 (5H, m), 6.85 (1H, dd, J=8.4 and 0.8 Hz), 6.76 (1H, dd, J=8.4 and 0.8 Hz) 6.06 (1H, s), 3.05 (2H, t, J=7.0 Hz), 2.92 (2H, t, J=6.8 Hz); $^{13}$C-NMR (100 MHz, $CDCl_3$) δ 183.5, 169.8, 160.8, 156.7, 139.4, 135.1, 128.7, 128.2, 126.6, 111.2, 110.6, 108.8, 106.6, 36.0, 32.8.

5-hydroxy-2-(2-hydroxyphenethyl)-4H-chromen-4-one (22b) Purification was done by stirring the crude solid in minimal dichloromethane and collecting the undissolved solid. IR $cm^{-1}$ 3153, 2944, 1650, 1618, 1487, 1583, 1259, 845, 801; $^1$H-NMR (400 MHz, DMSO-$d_6$): δ 12.63 (1H, br. s, 5-OH), 9.48 (1H, br. S. 2'-OH), 7.62 (1H, t, J=8.32 Hz), 7.08-699 (3H, m), 6.78 (2H, t, J=8.4 Hz), 6.69 (1H, t, J=7.4 Hz) 6.23 (1H, s), 2.95 (4H, s,); $^{13}$C-NMR (100 MHz, DMSO-$d_6$) δ 182.9, 171.4, 159.9, 156.2, 155.2, 135.6, 129.8, 127.4, 125.8, 118.8, 114.9, 110.7, 109.8, 108.1, 107.0, 33.5, 27.0.

7-hydroxy-2-phenethyl-4H-chromen-4-one (22k) Purified by column chromatography by elution with 95/5 dichloromethane/MeOH. IR $cm^{-1}$ 3026, 1621, 1548, 1495, 1421, 1256, 852, 823; $^1$H-NMR (400 MHz, acetone-$d_6$): δ 9.45 (1H, s, 7-OH), 7.96-7.90 (1H, m) 7.28-7.18 (5H, m,), 6.94 (1H, d J=8.68 Hz), 6.87 (1H, s), 6.00 (1H, s), 3.08 (2H, t, J=7.76 Hz), 2.95 (2H, t, J=6.08 Hz); $^{13}$C-NMR (100 MHz, acetone-$d_6$) δ 177.2, 168.7, 163.1, 159.1, 141.2, 129.29, 129.26, 127.7, 127.1, 117.8, 115.2, 110.3, 103.3, 36.2, 33.4.

Results

Figure 4:
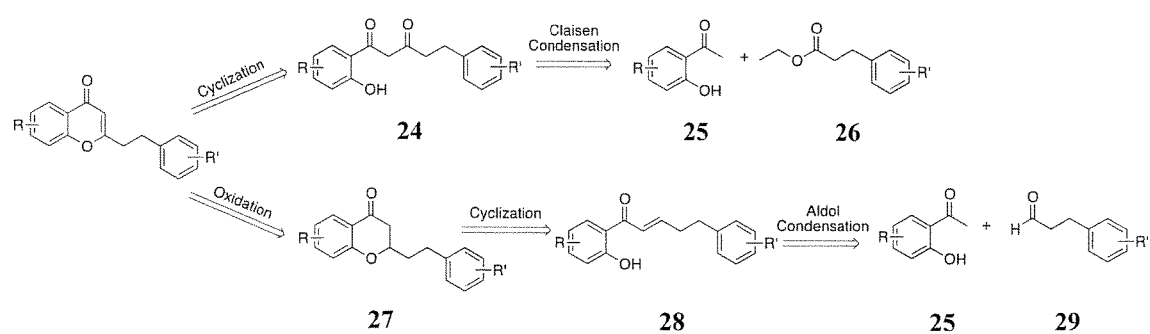
FIG. 4. Retrosynthetic analysis for 2-(2-phenylethyl) chromone analogues.
Figure 5:
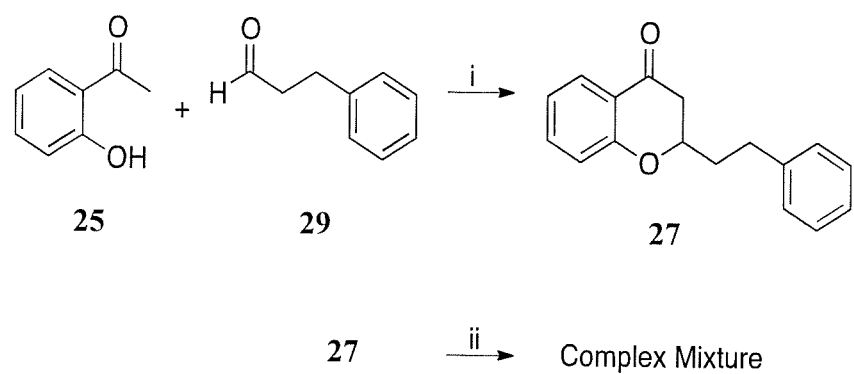
FIG. 5. Synthesis of 9 using aldol condensation conditions. Reagents and conditions: (i) Piperdine (cat), EtOH, reflux, 24 h, 50% (ii) DMSO, I$_2$, 140° C. 1 h.

Retrosynthetic analysis of chromones 5, 9, 10, 22b, 22k, and 23 indicates the key intermediate 24 or 28 prepared through the corresponding aldol or Claisen condensation should be suitable to afford the desired chromones (FIG. 4). Past literature has shown that the condensation of aromatic aldehydes with 2'-hydroxyacetophenones (25) under aldol conditions leads to spontaneous cyclization to afford intermediates as of 27.[32] This domino reaction was considered advantageous as oxidation of 27 would yield the desired 2-(2-phenylethyl)chromone in as few as two steps. Accordingly, 2'-hydroxyacetophenone 25 was condensed with hydrocinnamaldehyde (29) to afford the cyclized product 27 in 50% yield (FIG. 5). Although in the initial trial, it was anticipated that oxidation of 27 with iodine in refluxing DMSO[33] would afford the desired product, such conditions gave only a complex mixture. Other methodologies to affect this transformation were not pursued, as they would each involve multiple reaction steps.

Given the difficulties associated with oxidation of 27, the alternative route utilizing the cyclization of 1,3-diones (24) was pursued. The construction of these diones for chromone synthesis is typically accomplished using the Baker-Venkataraman rearrangement.[31] While this can be an effective strategy, the synthesis of the precursor benzoate ester is not trivial when the dihydroxyacetophenone needed for the synthesis of 10, 22b, and 22k are adopted as the starting reagent. Therefore, it was decided to use the direct Claisen condensation of acetophenone 25 with ester 26. This idea had been explored in a previous report on the synthesis of 10 but only very low yields (<9%) of the condensation product were obtained.[34] Thus, this work sought to improve the application of the Claisen condensation for the synthesis of natural products 5, 9, 10, 22b, 22k, and 23.

Figure 6:
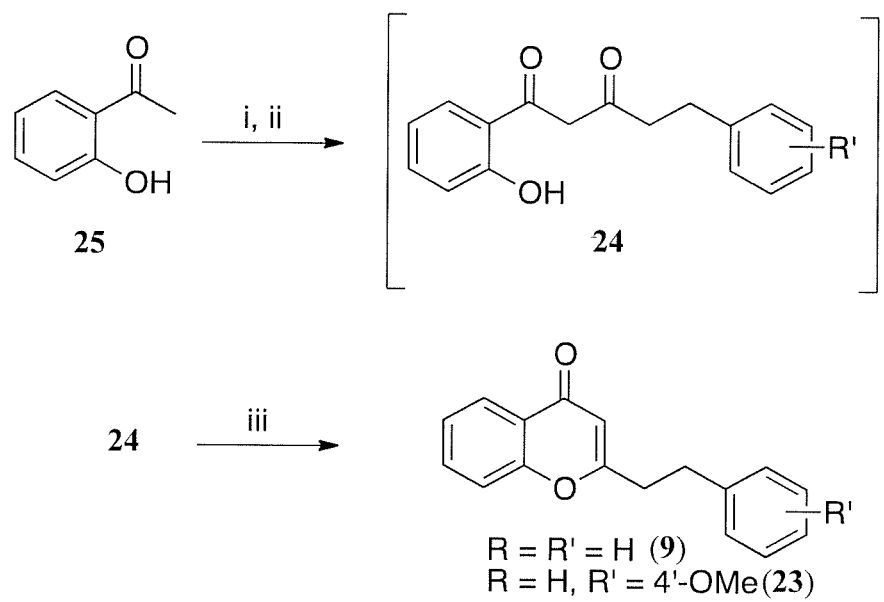
FIG. 6. Synthesis of 2-(2-phenylethyl)chromones 9 and 23 utilizing the Claisen condensation. Reagents and conditions: (i) NaH, THF, reflux, 1 h. (ii) 10, THF, rt, 24 h (iii) AcOH or MeOH, HCl (cat.) reflux 45 min.
Figure 7:
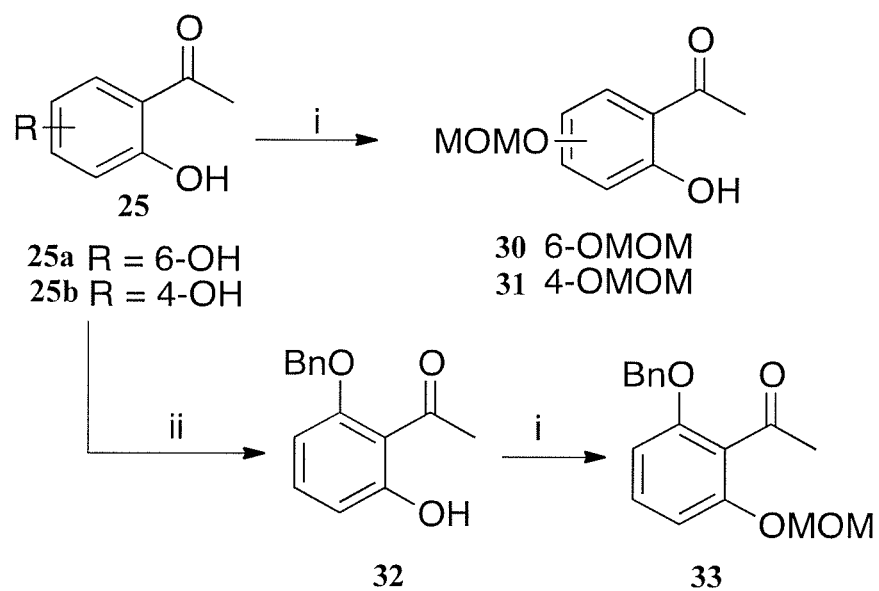
FIG. 7. Protection of dihydroxyacetopheones. Reagents and conditions: (i) Diisopropylethylamine, CH$_2$Cl$_2$, MOMCl, rt, 1 h. (ii) BnBr, K$_2$CO$_3$, KI, acetone, reflux, 16 h.
Figure 8:
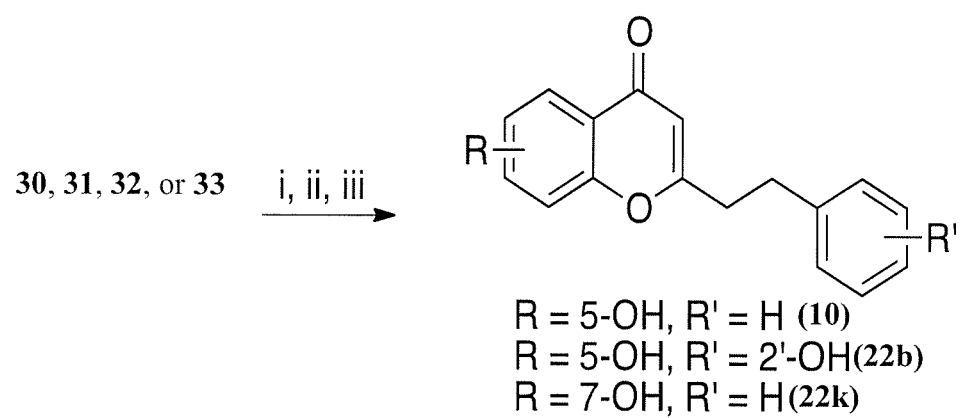
FIG. 8. Synthesis of 2-(2-phenylethyl)chromones 10 and 22b. Reagents and conditions: (i) NaH, THF, reflux 1 h. (ii) 10, THF, reflux, 4 h (iii) MeOH, HCl (cat.), reflux, 45 min.

Due to the enolizable nature of both the ketone and ester, it was expected that optimal yields of the Claisen condensation would be achieved if preformation of the enolate from 25 were accomplished. Consequently, 25 was added drop wise to a refluxing slurry of sodium hydride (NaH). After refluxing for 1 h the solution was allowed to cool to room temperature and the ester (26) was added drop wise and the solution stirred overnight (FIG. 6). Based on previous studies, it was anticipated that the crude Claisen condensation product (24) could be used directly for cyclization without purification.[35] Hence, the efficiency of the Claisen condensation would be judged on the yield of the final product. Accordingly, the crude 1,3-dione (24) was cyclized by refluxing in acetic acid with trace amounts of HCl to yield 9 in 73% yield after purification (Table 2, Entry 1).

previous attempts on the synthesis of 10 through a direct Clasien condensation approach, were postulated to be the fact of both hydroxyl groups being unprotected. Therefore, we hypothesized that incorporation of a protecting group for one or both of the hydroxyl groups should allow a smoother Claisen condensation. Therefore, 2,6-dihydroxyacetophenone 25a was monoprotected as either the methoxymethyl ether 30 or the benzyl ether 32 (FIG. 7).[33,38] Benzyl ether 32 was then further protected with MOMCl to provide 33. These protecting groups were selected as they should both be cleaved during the acidic cyclization step simultaneously.[36] Following the above described methodology for the Claisen condensation, acetophenone 30 was used to prepare chromone 10 in 43% yield over three steps (FIG. 8, Table 2, Entry 3). Use of the benzyl ether protected acetophenone 31 led to an increase in yield to 52% after purification (Table 2, Entry 4). These results represent a significant improvement over previous attempts utilizing the direct Claisen condensation approach for the synthesis of 2-(2-phenylethyl) chromones.[34] It was concluded that the improvement in yield was attributed to the monoprotection of 25. It was hoped then that protection of both hydroxyl groups would further improve the yield. However, when using 33 as the starting acetophenone, the Claisen condensation did not take place (Table 2, Entry 6). This might be due to steric hindrance to the methyl group of the ketone to prevent enolate formation.

Interestingly when the order of addition was changed such that 30 was added to a refluxing solution of 29, a significant decrease in the yield was observed (Table 2, Entry 5).

In addition to changes in the order of addition and introduction of protecting groups, alternative bases were also explored to further improve the yield. Adoption of

TABLE 2

Reaction conditions explored to optimize yields.

| Entry | Base | Acetophenone | Ester (26) R'= | Claisen Condensation Conditions | Cyclization Conditions | Product | Yield (%) |
|---|---|---|---|---|---|---|---|
| 1 | NaH | 25 | H | A | HCl/AcOH/Reflux | 9 | 73 |
| 2 | NaH | 25 | 4-OMe | A | HCl/MeOH/Reflux | 23 | 55 |
| 3 | NaH | 30 | H | A | HCl/AcOH/Reflux | 10 | 43 |
| 4 | NaH | 32 | H | A | HCl/AcOH/Reflux | 10 | 52 |
| 5 | NaH | 30 | H | B | HCl/AcOH/Reflux | 10 | 24 |
| 6 | NaH | 33 | H | A | — | 10 | — |
| 7 | NaOMe | 30 | H | C | — | 10 | — |
| 8 | LDA | 30 | H | C | — | 10 | — |
| 9 | KOtBu | 30 | H | C | — | 10 | — |
| 10 | NaH | 30 | H | A | HCl/MeOH/Reflux | 10 | 40 |
| 11 | NaH | 30 | H | A | HCl(xs)/MeOH/rt | 10 | 15 |
| 12 | NaH | 32 | 2-OMOM | A | — | 22b | — |
| 13 | NaH | 32 | 2-OMOM | D | HCl/AcOH/Reflux | 22b | — |
| 14 | NaH | 30 | 2-OMOM | D | HCl/MeOH/Reflux | 22b | 83 |
| 15 | NaH | 30 | H | D | HCl/MeOH/Reflux | 10 | 80 |
| 16 | NaH | 31 | H | D | HCl/MeOH/Reflux | 22k | 73 |

Continuing with this approach, attention was turned to the synthesis of 23. The highly acidic and elevated temperatures used for the cyclization to provide 9 would very likely lead to the hydrolysis of the methoxy substituent of 23.[36] On the other hand, another cyclization strategy using refluxing methanol with trace HCl has been reported to give comparable yields to that of refluxing acetic acid.[37] When applying this methodology, 23 was prepared in 55% yield over 3 steps after purification (Table 2, Entry 2).

The synthesis of 9 and 23 demonstrate the feasibility of the direct Clasien condensation approach for the synthesis of 2-(2-phenylethyl)chromones. The low yields associated with 'BuOK or NaOMe did not provide any of the desired products and only the starting materials were recovered after workup. This may be attributed to the insolubility of these salts in THF. The use of LDA did show consumption of the starting material; however, after reaction workup only a complex mixture of products was obtained. Thus, NaH seemed to be optimal.

In the synthesis of 23, the cyclization solvent was changed from acetic acid to methanol. The impact of this change on yield was also investigated for the synthesis of 10. Refluxing in methanol provided yields comparable to those of acetic acid (Table 2, Entry 10). Cyclization in methanol at room temperature[39], however, gave significantly reduced yields (Table 2, Entry 11).

Based on the above results, the synthesis of 22b was then undertaken. When the Claisen condensation was carried out at room temperature using acetophenone 32 and the MOM protected ester 26, no reaction was observed. Previous studies have shown that the Claisen condensation can be carried out at elevated temperatures when sterically crowded substrates are used.[40] Based on this, after preformation of the enolate, the solution was maintained at reflux and the ester was added drop wise and the reaction mixture allowed to reflux for another 4 h. Thin Layer Chromatography (TLC) of this reaction showed consumption of starting acetophenone 32 and the appearance of a new fluorescent spot, which was presumed to be the condensation product. However, refluxing this crude Claisen condensation product in acetic acid produced an extremely complex mixture by TLC (Table 2, Entry 13). In response, the monoprotected acetophenone 30 was used in the Claisen condensation under refluxing conditions. Again consumption of the starting material was observed along with the appearance of a new fluorescent spot. This crude product was then cyclized in refluxing methanol and upon purification 22b was isolated in 83% yield. The high yield of this reaction prompted a revisit to the synthesis of 10. Utilizing the refluxing Claisen condensation conditions and methanol for the cyclization solvent the yield of 10 was also increased to 80%. Finally, using these optimized conditions 2,4-dihydroxyacetophenone 25b was converted to 2-(2-phenylethyl)chromone 22k in 73% overall yield.

CONCLUSION

In summary, an efficient and rapid route has been developed and applied to the synthesis of five naturally occurring 2-(2-phenylethyl)chromones 5, 9, 10, 22b, 22k, and 23. Monoprotection of the starting dihydroxyacetophenones was proven to be critical for improving the yield of the Claisen condensation. Sodium hydride was shown to be the most effective base to execute the Claisen condensation. Carrying out the Condensation at reflux significantly reduced reaction time while simultaneously increasing the yield. Furthermore, this methodology can be used for the synthesis of 2-(2-phenylethyl)chromones bearing substitutions on both phenyl rings. Thus, this approach allows for the convenient syntheses of a structurally diverse compound library.

Example 2. Characterization of 5-Hydroxy-2-(2-Phenylethyl)Chromone (5-HPEC), a Novel Non-Nitrogenous Ligand for 5-HT$_{2B}$ Receptor Introduction The 5-HT$_{2B}$ receptor ligand 5-HPEC (10) contains fewer hydroxyl groups than other naturally-occurring neuroprotective chromones, such as Kaempferol.[41] This observation led to the discovery that the neuroprotective effects of 5-HPEC are related to its ability to selectively bind 5-HT$_{2B}$ receptors in the CNS and PNS. Example 2 is a method for preparation of 5-HPEC and demonstrates that 5-HPEC selectively binds and antagonizes 5-HT$_{2B}$ receptors that mediate its biological activity in the CNS.

Materials and Methods

Chemical Synthesis:

General Procedure for the preparation of 5-Hydroxychromones: To a slurry of sodium hydride (4.0 mmol) at reflux in THF was added drop wise over 10 min the acetophenone (1.0 mmol) which was dissolved in 10 mL of THF. The solution was then allowed to reflux for 1 h past the addition of the last drop. While still at reflux, the appropriate ester (1.5 mmol) was then added drop wise over 15 min and the resulting solution stirred at reflux for 4 h. The reaction mixture was then poured over 50 mL of saturated NH$_4$Cl while still hot and extracted three times with ethyl acetate. The combined organic layers were dried over Na$_2$SO$_4$ and concentrated to yield the crude Claisen product. Without purification the Claisen product was then dissolved in 20 mL of methanol. While vigorously stirring 15 drops of concentrated HCl were added and the solution placed in an oil bath that was preheated to 90° C. and refluxed for 45 min. After cooling to room temperature saturated Na$_2$CO$_3$ was added until the pH was neutral by pH paper. Next 50 mL of ethyl acetate was added. The organic layer was washed with water (25 mL), Brine (25 ml), dried over Na$_2$SO$_4$ and concentrated to give the crude 5-Hydroxychromone products which were purified by the appropriate measure.

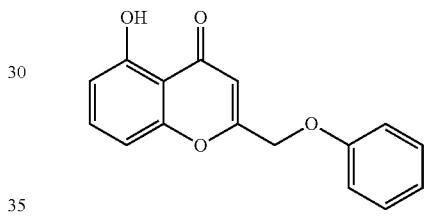

5-hydroxy-2-(phenoxymethyl)-4H-chromen-4-one (22a): Purified by Column chromatography eluting with 3:1 dichloromethane:hexanes and precipitation from acetone (20% yield). IR (diamond cm$^{-1}$) 3082, 2903, 1655, 1628, 1497, 1431, 1384, 1240, 863, 803; $^1$H-NMR (400 MHz, DMSO-d$_6$): δ, 12.47 (1H, s), 7.67 (1H, t J=8.36 Hz), 7.34 (2H, dt, J=2.04 and 8.72 Hz), 7.11-6.99 (4H, m), 6.84 (1H, dd J=7.6 and 8.24 Hz) 6.54 (1H, s), 5.17 (2H, s); $^{13}$C-NMR (100 MHz, DMSO-d$_6$) δ 182.8, 166.1, 159.9, 157.3. 156.0, 136.1, 129.6, 121.6, 114.8, 111.1, 110.1, 108.1, 107.3, 65.3; MS (positive) m/z 267.0664[M$^+$] (calcd for C$_{16}$H$_{12}$O$_4$, 267.0063).

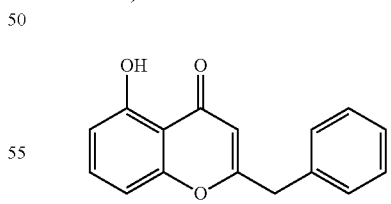

2-benzyl-5-hydroxy-4H-chromen-4-one (22g): Purified by Column chromatography eluting with 80/20 Hexanes/Ethyl Acetate (50% yield). IR (diamond cm$^{-1}$) 3098, 3055, 2788, 1667, 1618, 1482, 1434, 1372, 1263, 864, 820; $^1$H-NMR (400 MHz, Acetone-d$_6$): δ, 12.62 (1H, s), 7.569 (1H, t, J=8.4 Hz), 7.43-7.28 (5H, m), 6.89 (1H, dd, J=0.68 and 8.48 Hz), 6.72 (1H, dd J=0.52 and 8.24 Hz) 6.16 (1H, s), 4.05 (1H, s); $^{13}$C-NMR (100 MHz, Acetone-d$_6$) δ 184.4, 171.2, 161.8, 157.7, 136.4, 136.2, 130.1, 129.7, 128.2, 111.7, 111.1, 109.6, 107.7, 40.8. HREIMS (positive) m/z 251.0747 [M⁺] (calcd for $C_{16}H_{12}O_3$, 251.0714).

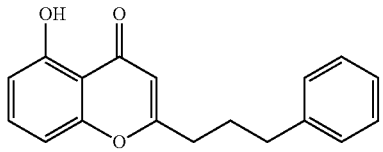 [SMILES: O=c1cc(CCCc2ccccc2)oc2cccc(O)c12]

5-hydroxy-2-(3-phenylpropyl)-4H-chromen-4-one (22h): Purified by Column chromatography eluting with 80/20 Hexanes/Ethyl Acetate (90% yield). IR (diamond cm⁻¹) 3025, 2930, 1652, 1618, 1475, 1459, 1367, 1252, 845, 802; ¹H-NMR (400 MHz, CDCl₃): δ, 12.54 (1H, s), 7.47 (1H, t, J=8.32 Hz), 7.31-7.17 (5H, m), 6.83 (1H, dd, J=0.64 and 8.4 Hz), 6.77 (1H, d, J=8.24 Hz) 6.09 (1H, s), 2.72 (2H, t, J=7.4 Hz), 2.62 (2H, t, J=7.32), 2.07 (2H, p, J=7.72 Hz); ¹³C-NMR (100 MHz, CDCl₃) δ 184.5, 170.6, 160.8, 156.7, 140.7, 135.0, 128.5, 128.4, 126.2 111.1, 110.6, 108.5, 106.8, 34.9, 33.6, 28.2. HREIMS (positive) m/z 279.1040 [M⁺] (calcd for $C_{18}H_{16}O_3$, 279.1023).

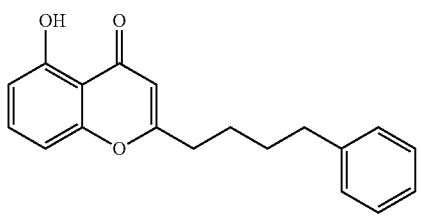 [SMILES: O=c1cc(CCCCc2ccccc2)oc2cccc(O)c12]

5-hydroxy-2-(4-phenylbutyl)-4H-chromen-4-one (22i): Purified by Column chromatography eluting with 70/30 Hexanes/Ethyl Acetate (70% yield). IR (diamond cm⁻¹) 3061, 2933, 2852, 1650, 1621, 1478, 1459, 1382, 1366, 1258, 873, 803; ¹H-NMR (400 MHz, Acetone-d₆): δ, 12.70 (1H, s), 7.59 (1H, t, J=8.32 Hz), 7.28-7.14 (5H, m), 6.95 (1H, dd, J=0.68 and 8.4 Hz), 6.74 (1H, d, J=8.28 Hz) 6.20 (1H, s), 2.77-2.67 (4H, m), 1.83-1.74 (4H, m); ¹³C-NMR (100 MHz, Acetone-d₆) δ 184.5, 172.6, 161.8, 157.7, 143.0, 136.2, 129.2, 129.1, 126.6 111.6, 111.1, 109.0, 107.7, 36.0, 34.5, 31.5, 27.0; HREIMS (positive) m/z 293.1196 [M⁺] (calcd for $C_{19}H_{18}O_3$, 293.1183).

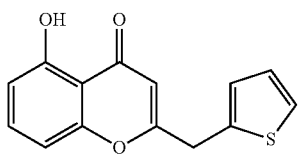 [SMILES: O=c1cc(Cc2cccs2)oc2cccc(O)c12]

5-hydroxy-2-(thiophen-2-ylmethyl)-4H-chromen-4-one (22r): Purified by Column chromatography eluting with 70/30 Hexanes/Ethyl Acetate (40% yield). IR (diamond cm⁻¹) 3061, 2933, 2852, 1650, 1621, 1478, 1459, 1382, 1366, 1258, 873, 803; ¹H-NMR (400 MHz, Acetone-d₆): δ, 12.58 (1H, s), 7.60 (1H, t, J=8.36 Hz), 7.39 (1H, dd J=1.16 and 5.12 Hz), 7.12 (1H, dd, J=0.88 and 3.4 Hz), 7.03 (1H, dd, J=3.48 and 5.12 Hz) 6.96 (1H, dd J=0.68 and 8.44 Hz), 6.74 (1H, dd, J=0.52 and 8.24 Hz), 6.24 (1H, s) 4.29 (1H, s); ¹³C-NMR (100 MHz, Acetone-d₆) δ 184.4, 170.1, 161.8, 157.6, 137.3, 136.5, 128.3, 128.1, 126.4 111.8, 111.1, 109.3, 107.8, 34.8; HREIMS (positive) in/z 257.0273 [M⁺] (calcd for $C_{14}H_{10}O_3S$, 257.0278).

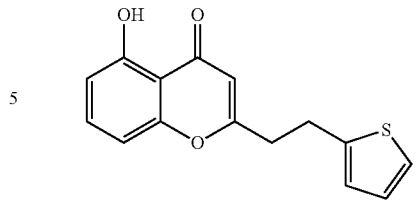

5-hydroxy-2-(2-(thiophen-2-yl)ethyl)-4H-chromen-4-one (22e): Purified by Column chromatography eluting with 50/50 hexanes/dichloromethane (30% yield). IR (diamond cm⁻¹) 3103, 3066, 2913, 1645, 1613, 1474, 1439, 1379, 1357, 1239, 840, 807 ¹H-NMR (400 MHz, Acetone-d₆): δ, 12.64 (1H, s), 7.61 (1H, t, J=8.36 Hz), 7.25 (1H, dd, J=2.16 and 4.2), 6.99 (1H, dd, J=0.72 and 8.44 Hz), 6.93-6.91 (2H, m) 6.75 (1H, dd, J=0.6 and 8.28), 6.22 (1H, s) 3.35 (2H, t, J=7.24 Hz), 3.09 (2H, t, J=7.64); ¹³C-NMR (100 MHz, Acetone-d₆) δ 184.3, 170.9, 161.8, 157.7, 143.1, 136.3, 127.8, 126.0, 124.7 111.7, 111.1, 109.6, 107.8, 36.7, 27.4; HREIMS (positive) m/z 271.0436 [M⁺] (calcd for $C_{15}H_{12}O_3S$, 271.0434).

Molecular modeling procedure: Gasteiger-Hückel charges were assigned to the molecular structures of 5-HT and 5-HPEC before energy minimization (10,000 iterations) with the TAFF within SYBYL-X2.0. The generic algorithm docking program GOLD 5.1 was used to perform the docking studies on X-ray crystal structure of agonist bound 5-HT$_{2B}$ receptor (PDB ID 4IB4) with standard default settings. The binding site was defined to include all atoms within 10 Å of the γ-carbon atom of Asp135. Based on the fitness scores and the binding orientation of each ligand within the binding cavity, the best GOLD-docked solution was selected and merged into the receptor. The combined receptor-ligand structures were then energy-minimized to optimize the interactions between ligand and receptor by removing structural clashes and minimizing strain energy. These optimized models were then subjected to hydropathic analysis with the HINT program. Pictures depicting docking poses were generated using PyMOL Molecular Graphics System, V1.5.0.4.

Results

Figure 9:
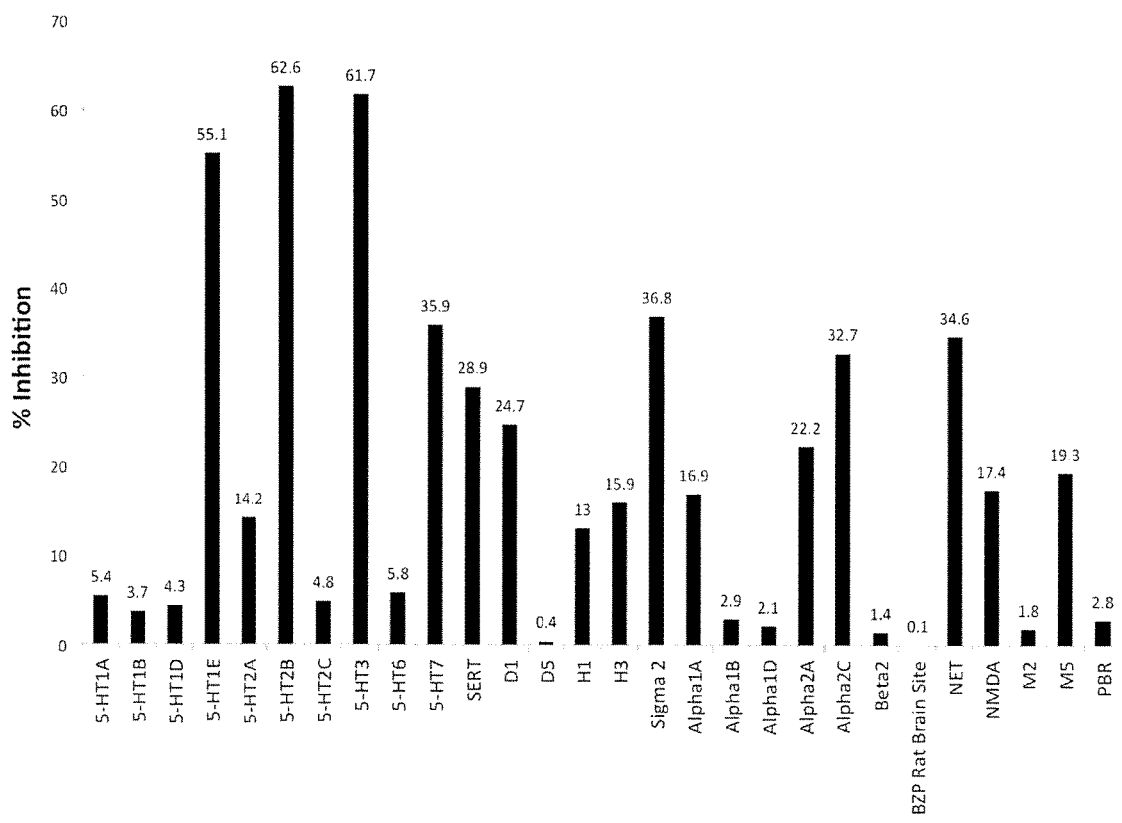
FIG. 9. Inhibitory response produced by 5-HPEC at various CNS receptors.

The initial screening measured the inhibition by 5-HPEC (at 10 μM) to radioligand binding on a series of selected receptors and ion channels. Inhibition of 50% or greater at this concentration was deemed meaningful. As shown in FIG. 9, 5-HPEC demonstrated inhibitory response at several serotonin (5-HT) receptors, namely 5-HT$_{1E}$, 5-HT$_{2B}$, and 5-HT$_3$, with inhibitory activities of 55%, 62%, and 61% respectively. Very low inhibitory effects were measured on other receptors from the 5-HT$_2$ subfamily, e.g. 5-HT$_{2A}$ (14.2%) or 5-HT$_{2C}$ (4.8%). These data demonstrate that 5-HPEC is a selective ligand for 5-HT$_{2B}$ over other receptors in the 5-HT$_2$ subfamily.

Following this initial investigation, the binding affinity of 5-HPEC at these identified receptors was determined (Table 3). The affinity of 5-HPEC at the 5-HT$_{1e}$ receptor seemed to be insignificant. On the other hand, 5-HPEC showed almost equal affinity on both 5-HT$_3$ and 5-HT$_{2B}$ receptors with pK$_i$ values of 5.60 and 5.61 respectively. These results are consistent with the role of serotonergic pathways in CNS neuroprotection.[42-44] These findings are also consistent with the neuroprotective properties observed by others using other classes of antagonists to 5-HT$_{2B}$ and 5-HT$_3$ receptors.[8,45]

TABLE 3

Determined pK$_i$ values for 5-HPEC at 5-HT$_{1E}$, 5-HT$_{2B}$, and 5-HT$_3$.

| Receptor | pK$_i^a$ |
|---|---|
| 5-HT$_{1E}$ | <5 |
| 5-HT$_{2B}$ | 5.61 ± 0.1 |
| 5-HT$_3$ | 5.60 ± 0.08 |

$^a$pK$_i$ were determined by competitive inhibition of [$^3$H]5-HT, [$^3$H]LSD, [$^3$H]GR65630 at 5-HT$_{1E}$, 5-HT$_{2B}$, and 5-HT$_3$ respectively. Concentration of the radioligand was equal to the K$_d$ of the radioligand which was determined by finding the mean for 3 previously conducted saturation binding assays.

Example 3. Functional Activity of 5-HPEC

The functional activity of 5-HPEC at 5-HT$_{2B}$ was studied to demonstrate the degree of selectivity at 5-HT$_{2B}$ over 5-HT$_{2A}$ and 5-HT$_{2C}$ and to confirm lack of toxicity and absence of agonist activity at the 5-HT$_{2B}$ receptor, since 5-HT$_{2B}$ agonists are known to contribute to valvular heart disease.[46] A calcium mobilization assay in Flp-In HEK cells using 5-HPEC at 10 μM showed minimal agonist activity (0.6±0.2% of the maximal response) when compared to 5-HT. Conversely, when challenged with an EC$_{50}$ dose (1.6 nM) of 5-HT, 5-HPEC demonstrated antagonist activity (6.9±1.9% inhibition). These data confirm that 5-HPEC is an antagonist rather than an agonist to the 5-HT$_{2B}$ receptor. A subsequent concentration response curve in the presence of an EC$_{50}$ concentration of 5-HT gave a pIC$_{50}$ value of 5.05±0.05 for 5-HPEC at the 5-HT$_{2B}$ receptor.

FIG. 10 shows serotonin (34) and three 5-HT$_{2B}$ antagonists. Based on the prior art, ligands targeting the 5-HT receptors and transporters required an amino moiety in order to facilitate ligand binding.[10] While some non-nitrogenous compounds have more recently demonstrated high affinity for the 5-HT transporter, no such ligand has ever been reported for the 5-HT$_{2B}$ receptor prior to this invention, and 5-HPEC represents a structurally unique non-nitrogenous 5-HT$_{2B}$ ligand.[47] To analyze the binding mode of 5-HPEC on the 5-HT$_{2B}$ receptor, an automated docking experiment was performed using a newly available agonist-bound X-ray crystal structure of 5-HT$_{2B}$.[48] A generic algorithm docking program GOLDv51 was used to acertain docking poses for both 5-HT and 5-HPEC. The generated binding modes were then re-scored using Hydropathic INTeraction (HINT)® that calculates free energy associated with non-bonded interactions based on a natural force field generated by employing experimentally determined partition co-efficients (Table 4).[49] As shown in FIGS. 11A and 11B, the highest scored 5-HT binding mode in the receptor indicated that the indole ring of 5-HT located in a hydrophobic pocket between helices 3 and 6. The indole nitrogen atom and the hydroxyl group interacted via hydrogen bonding with Thr140 and Ser222, respectively. The terminal amino group was shown to interact with Asp135 and Ser139. These data regarding binding mode for 5-HT were consistent with previously reported site-directed mutagenesis studies.[50]

TABLE 4

The optimal docking scores of 5-HT (34) and 5-HPEC (10) in the 5-HT$_{2B}$ receptor crystal structure.

| Compound | HINT | ChemPLP |
|---|---|---|
| 5-HT | 2669 | 59.44 |
| 5-HPEC | 537 | 50.75 |

In contrast, the best scored docking solution for 5-HPEC showed that its chromone core recognized a similar binding pocket compared to that of 5-HT, that is, between helices 3 and 6 Asp135 and Ser139 were involved in a potential hydrogen bonding network with the chromone hydroxyl group. Meanwhile, 5-HPEC interacted with a hydrophobic cavity around helix 7 and extracellular loop 2 lined with Leu362 and Leu209, which may further interact with the phenylethyl substituent of 5-HPEC. A qualitative comparison of the binding mode of 5-HPEC indicated less hydrogen bonding potential than 5-HT, which was reflected in its lower HINT score. This finding is consistent with the lower affinity of 5-HPEC (pK$_i$ 5.60) compared to 5-HT (pK$_i$ 7.87).[51] Recent reports have determined that structural changes within a ligand binding pocket can relatively subtle between agonist- and antagonist-bound protein.[52]

Example 4. Modification of 5-HPEC

Figure 12:
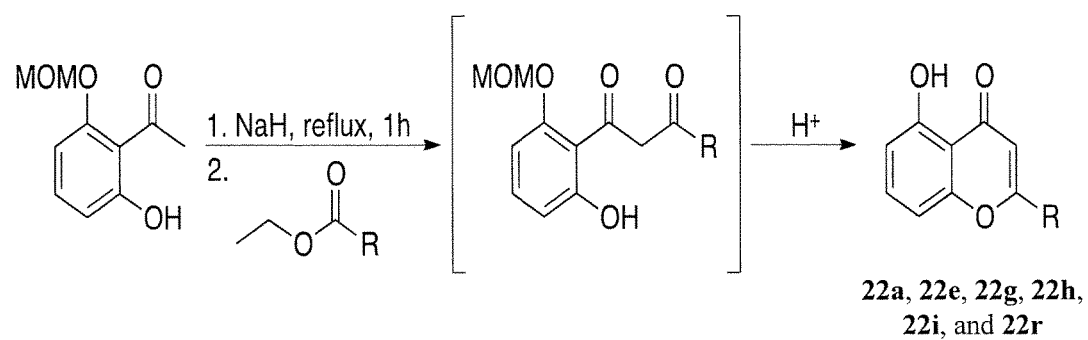
FIG. 12: Chemical synthesis route of 5-HPEC analogues.

It is an objective of the invention to identify modifications to the base structure of 5-HPEC that enhance selectivity and activation. To determine structural modifications that enhance or at least maintain the binding affinity of 5-HPEC to the 5-HT$_{2B}$ receptor, six analogues of 5-HPEC were synthesized (FIG. 12) and their inhibitory activity (at 10 μM) was assessed at each 5-HT$_2$ receptor (Table 5). The design of these analogues was focused on the effects of the alkyl chain length and the aromatic "C" ring on the affinity. The results of these modifications demonstrated that the nature of the alkyl chain is important to 5-HT$_{2B}$ selectivity and binding. For example, replacing C12 with an oxygen atom (22a) led to a decrease in activity, which means that a hydrocarbon chain would be preferred. Additionally, the alkyl chain length was found to be critical because extension of the alkyl chain by only one methylene group (22h) led to an increase in activity while any other changes in chain length were detrimental. Finally, exchanging the phenyl ring with a thiophene (22i) showed improved activity over the parent compound. None of the modifications gave rise to any significant affinity change at the 5-HT$_{2A}$ or 5-HT$_{2C}$ receptors, again demonstrating selectivity for the 5-HT$_{2B}$ receptor.

TABLE 5

Inhibitory activity of 5-HPEC analogues at the 5-HT$_2$ family of receptors.

| | | | % Inhibition | |
|---|---|---|---|---|
| Compound | R | 5-HT$_{2B}$ | 5-HT$_{2A}$ | 5-HT$_{2C}$ |
| 10 | 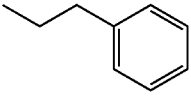 | 62.6 | 14.2 | 4.8 |

TABLE 5-continued

Inhibitory activity of 5-HPEC analogues at the 5-HT₂ family of receptors.

| Compound | R | 5-HT$_{2B}$ | % Inhibition 5-HT$_{2A}$ | 5-HT$_{2C}$ |
|---|---|---|---|---|
| 22a | -CH₂CH₂-O-phenyl | 50.0 | 0.2 | 7.8 |
| 22g | -CH₂CH₂-phenyl | 30.6 | 1.4 | 24.8 |
| 22h | -CH₂CH₂CH₂-phenyl | 70.4 | 5.4 | 7.9 |
| 22i | -CH₂CH₂CH₂CH₂-phenyl | 45.2 | 5.7 | 14.7 |
| 22r | -CH₂-(2-thienyl) | 31.5 | −4.5 | 23.5 |
| 22e | -CH₂CH₂-(2-thienyl) | 74.8 | 1.4 | 19.6 |

CONCLUSION

This example of the invention identifies selective binding to the 5-HT$_{2B}$ to mediate the biological activity of 5-hydroxy-2-(2-phenylethyl)chromone (5-HPEC) via CNS receptors, transporters, and ion channels. 5-HPEC demonstrated inhibitory activity at 5-HT receptors, namely 5-HT$_{1E}$, 5-HT$_{2B}$, and 5-HT$_3$. 5-HPEC is selective for 5-HT$_{2B}$ over others in the 5-HT$_2$ subfamily. In addition, 5-HPEC is an antagonist at 5-HT$_{2B}$ receptor in a calcium mobilization assay. Furthermore, docking studies utilizing the crystal structure of 5-HT$_{2B}$ identified a binding pocket for this novel ligand. Moreover, six analogues of novel non-nitrogenous 5-HPEC were synthesized and used to demonstrate that the composition and length of the alky chain contributes to selective binding of the 5-HT$_{2B}$ receptor, and that the aromatic "C" ring can be substituted for the more hydrophobic thiophene.

Example 5. Design, Synthesis, and Biological Evaluation of 5-Hydroxy-2-(2-Phenylethyl)Chromone Analogues as Novel Non-Nitrogenous 5-HT$_{2B}$ Ligands Introduction The 2-(2-phenylethyl)chromone: 5-hydroxy-2-(2-phenylethyl)chromone (5-HPEC, 10) has been shown to possess neuroprotective activity against glutamate excitotoxicity.[17] In this Example, the potential molecular basis leading to the activity of 5-HPEC was identified and used to design rational analogues that would selectively bind and antagonize 5-HT$_{2B}$ receptors in the CNS. As shown in the series of biological screenings of Example 2, 5-HPEC behaves as a selective antagonist at 5-HT$_{2B}$ with moderate affinity.[53] 5-HPEC was used as a unique scaffold for generating synthetic analogues and modifications for use as non-nitrogenous ligands for 5-HT$_{2B}$ that are useful as neuroprotective treatments.

Examples 3 and 4 identify important structural requirements needed to increase affinity while maintaining selectivity for 5-HT$_{2B}$. A series of non-natural 5-HPEC analogues were synthesized. The synthesis was based on the synthesis of 2-(2-phenylethyl)chromones in Example 1, with variations in the structural features of the compound.[22] The structural features varied were the nature of the aromatic "C" ring, alkyl chain length and composition at C2, substitution pattern of the "C" ring, and the substitution pattern of the "B" ring. Following syntheses, the compounds were screened for their ability to inhibit radioligand binding at each of the 5-HT$_2$ receptors at a single concentration. Those showing significant inhibition (>50%) were then further evaluated to determine binding affinity at the 5-HT$_{2B}$ receptor. Additionally, molecular modeling studies were performed to determine potential correlations between 2-(2-phenylethyl)chromone structure and 5-HT$_{2B}$ affinity.

Materials and Methods

General Procedure for the Fischer Esterification:

Sulfuric acid (4.0 mL, 122 mmol) was slowly added to a solution of the carboxylic acid (20.0 g, 122 mmol) in ethanol (150 mL) previously cooled to 0° C. on an ice bath. After warming to room temperature, the mixture heated to reflux and allowed to reflux for 16 h. After cooling to room temperature, the mixture was concentrated in vacuo at room temperature. The residue was then dissolved in ethyl acetate. The organic layer was washed three times with half the volume of saturated NaHCO$_3$. The organic layer was then washed with brine and dried over MgSO$_4$. The dried organic layer was then evaporated to dryness to produce the desired ester which was used in the claisen condensation without further purification.

Ethyl 2-phenylacetate (12a), Colorless oil $^1$H NMR (400 MHz, CDCl3, 30° C.) δ 7.33-7.23 (5H, m), 4.14 (2H, q, J=7.14 Hz), 3.59 (2H, s), 1.24 (3H, t, J=7.14 Hz); $^{13}$C NMR (CDCl3, 100 MHz): δ=171.60, 134.19, 129.26, 128.56, 127.05, 60.8, 41.5, 14.2

Ethyl 3-phenylpropanoate (12b), Colorless oil $^1$H NMR (400 MHz, CDCl3, 30° C.) δ 7.29-7.18 (5H, m), 4.12 (2H, q, J=7.14 Hz), 2.94 (2H, t, J=7.60 Hz), 2.61 (2H, t, J=7.56 Hz), 1.22 (3H, t, J=7.12 Hz); $^{13}$C NMR (CDCl3, 100 MHz): δ=172.9, 140.6, 128.5, 128.3, 126.2, 60.4, 35.9, 31.0, 14.2

Ethyl 4-phenylbutanoate (12c), Colorless oil. $^1$H NMR (400 MHz, CDCl3, 30° C.) δ 7.29-7.17 (5H, m), 4.12 (2H, q, J=7.13 Hz), 2.65 (2H, t, J=7.60 Hz), 2.32 (2H, t, J=7.5 Hz), 1.95 (2H, p, J=7.54 Hz), 1.25 (3H, t, J=7.08 Hz); $^{13}$C NMR (CDCl3, 100 MHz): δ=173.5, 141.5, 128.5, 128.4, 125.9, 60.3, 35.2, 33.7, 26.6, 14.3

Ethyl 5-phenylpentanoate (12d) Colorless oil $^1$H NMR (400 MHz, CDCl3, 30° C.) δ 7.29-7.15 (5H, m), 4.11 (2H, q, J=7.13 Hz), 2.62 (2H, t, J=7.10 Hz), 2.31 (2H, t, J=7.16 Hz), 1.66 (4H, m), 1.24 (3H, t, J=7.14 Hz); $^{13}$C NMR (CDCl3, 100 MHz): δ=173.7, 142.2, 128.4, 128.3, 125.8, 60.2, 35.6, 34.2, 30.9, 24.6, 14.3.

Ethyl 3-(thiophen-2-yl)propanoate (12e) Pale yellow oil. $^1$H NMR (400 MHz, CDCl3, 30° C.) δ 7.11 (1H, d, J=5.2 Hz), 6.91 (1H, dd, J=5.2, 3.4 Hz), 6.81 (1H, d, J=3.4 Hz), 4.14 (2H, q, J=7.13 Hz), 3.16 (2H, t, J=7.62), 2.67 (2H, t, J=7.62 Hz), 1.25 (3H, t, J=7.16 Hz); $^{13}$C NMR (CDCl3, 100 MHz): δ=172.5, 143.1, 126.8, 124.6, 123.5, 60.6, 36.2, 25.2, 14.2.

General Procedure for Protection with MOM:[38]

To a solution of phenol (4.0084 g, 32.8 mmol) and DIPEA (17.1 ml, 98.2 mmol) in CH$_2$Cl$_2$ (45 ml), MOMCl (4.0678 g, 50.5 mmol) was added at room temperature. This solution was stirred at room temperature for 1-2h. After the allotted time, water was added and the mixture and the aqueous layer was extracted with CH$_2$Cl$_2$. The organic layer was dried over Na$_2$SO$_4$, and concentrated. The residue was purified by chromatography over a column of silica gel in 50/50 DCM/Hexanes.

2-Methoxymethoxybenzaldehyde (13a): Spectral data was consistent with what was previously reported.[38]
3-Methoxymethoxybenzaldehyde (13b): Spectral data was consistent with what was previously reported.[38]
4-Methoxymethoxybenzaldehyde (13a) Spectral data was consistent with what was previously reported.[38] 2-Hydroxy-4-methoxymethoxyacetophenone (20a): Spectral data was consistent with what was previously reported.[38] 2-Hydroxy-6-methoxymethoxyacetophenone (20b): Spectral data was consistent with what was previously reported.[38]

Ethyl 3-(2-(methoxymethoxy)phenyl)propanoate (15a)

To a mixture of 13 (6.6 mmol) and Triethyl phosphonoacetate (6.0 mmol) was added DBU (8.2 mmol). The resulting mixture was stirred for 4 h at room temperature. The reaction was quenched with water (25 mL) and the aqueous layer extracted with ethyl acetate (20 mL, 3×). The organic layer was washed with brine, dried over NaSO$_4$, and concentrated to give the product as a crude reddish brown oil. This crude oil was filtered over a silica pad with 50/50 DCM/Hexane to remove the base line residue. The filtrate was then concentrated to give a light colored oil. This oil was then re-dissolved in ethanol (30 ml) and Pd/C (10 wt %) was added. The mixture was then hydrogenated at 60 p.si for 2 hours. The reaction was then filtered over celite and the celite washed with ethanol. After the filtrate was concentrated down. The resulting oil was purified on silica gel with 80/20 hexane/ethyl acetate to give the desired product as colorless oil. $^1$H NMR (400 MHz, CDCl3, 30° C.) δ 7.16 (2H, m), 7.05 (1H), 6.62 (1H), 5.29 (2H, s), 4.1 (2H, q, J=7.16), 3.483 (3H, s), 2.96 (2H, t, J=7.56), 2.61 (2H, t, J=7.56), 1.23 (3H, t, J=7.12 Hz)$^{13}$C NMR (CDCl3, 100 MHz): δ=173.3, 155.1, 130.0, 129.4, 127.6, 121.6, 113.7, 94.2, 60.3, 56.0, 34.4, 26.1. 14.2

Ethyl 3-(3-(methoxymethoxy)phenyl)propanoate (15b)

Colorless oil. Prepared in the same manner as 15a. $^1$H NMR (400 MHz, CDCl3, 30° C.) $^1$H NMR (400 MHz, CDCl3, 30° C.) δ 7.17 (1H, m), 6.87 (3H, m), 5.15 (2H, s), 4.13 (2H, q, J=7.12), 3.47 (3H, s), 2.92 (2H, t, J=7.60), 2.61 (2H, t, J=7.52) 1.23 (3H, t, J=7.12) $^{13}$C NMR (CDCl3, 100 MHz): δ=172.8, 157.4, 142.2, 129.4, 121.8, 116.3, 114.0, 94.5, 60.4, 55.9, 35.8, 30.9, 14.2

Ethyl 3-(4-(methoxymethoxy)phenyl)propanoate (15c)

Colorless oil. Prepared in the same manner as 15a. $^1$H NMR (400 MHz, CDCl3, 30° C.) $^1$H NMR (400 MHz, CDCl3, 30° C.) δ 7.12 (2H, d, J=8.5), 6.96 (2H, d, J=8.6), 5.14 (2H, s), 4.13 (2H, q, J=7.16), 3.46 (3H, s), 2.89 (2H, t, J=7.60), 2.58 (2H, t, J=7.52) 1.23 (3H, t, J=7.12) $^{13}$C NMR (CDCl3, 100 MHz): δ=172.9, 155.6, 134.0, 129.2, 116.3, 94.5, 60.3, 55.9, 36.1, 30.1, 14.2.

Ethyl 2-phenoxyacetate (17)

To a slurry of N,N'-carbonyldimidazole in anhydrous THF was added a solution of phenoxyacetic acid 16 in anhydrous. Upon addition, rapid effervescence was observed. This solution was allowed to stir for 30 min past the end of effervescence. At this time absolute ethanol was added and the mixture allowed to stir at room temperature for 16 hours. The mixture was then concentrated down and the residue taken up in dichloromethane. The organic layer was washed three times with half the volume of saturated NaHCO$_3$. The organic layer was then washed with brine dried over MgSO$_4$ and concentrated to give the desired product as a colorless oil. $^1$H NMR (400 MHz, CDCl3, 30° C.) δ 7.28 (2H, dd J=3.0 and 1.8 Hz), 6.97 (1H, t, J=3.1 Hz), 6.89 (2H, d, J=2.00 Hz), 4.61 (2H, s), 4.26 (2H, q, J=7.15), 1.29 (3H, t, J=7.13 Hz); $^{13}$C NMR (CDCl3, 100 MHz): δ=168.9, 157.8, 129.6, 121.7, 114.7, 65.4, 61.3, 14.2.

Ethyl 2-(benzyloxy)acetate (19)

To a slurry of Sodium Hydride (60% dispersion, mmol) cooled to −10° C. was added benzyl alcohol (mmol) drop wise over 5 min. This solution was allowed to stir at this temperature for 1 hr. Following this, Ethyl-2-bromoacetate (mmol) was added. The solution was then allowed to adjust to room temperature and stir at room temperature for 20 h. The reaction mixture was then concentrated down. The residue was taken up in ethyl acetate. The organic layer was washed with NaHCO$_3$ and brine. After drying over Na$_2$SO$_4$ the organic layer was concentrated to give a crude pale yellow oil. The oil was purified over silica gel by eluting with 50/50 DCM/Hexanes to give the pure product as a colorless oil. $^1$H NMR (400 MHz, CDCl3, 30° C.) δ 7.36-7.33 (5H, m), 4.63 (2H, s), 4.22 (2H, t, J=7.13 Hz), 4.08 (2H, s), 1.28 (3H, t, J=7.16); $^{13}$C NMR (CDCl3, 100 MHz): δ=170.3, 137.2, 128.5, 128.1, 128.0, 73.3, 67.3, 60.8, 14.2.

General Procedure for the Preparation of 5/7-Hydroxychromones

To a slurry of sodium hydride (4.0 mmol) at reflux in THF was added drop wise over 10 mm the acetophenone 21 (1.0 mmol) which was dissolved in 10 mL of THF. The solution was then allowed to reflux for 1 h past the addition of the last drop. While still at reflux, the appropriate ester (12, 15, 17, or 19) (1.5 mmol) was then added drop wise over 15 min and the resulting solution stirred at reflux for 4 h. The reaction mixture was then poured over 50 mL of saturated NR$_4$Cl while still hot and extracted three times with ethyl acetate. The combined organic layers were dried over Na$_2$SO$_4$ and concentrated to yield the crude Claisen product. Without purification the Claisen product was then dissolved in 20 mL of methanol. While vigorously stirring, 15 drops of concentrated HCl were added and the solution placed in an oil bath that was preheated to 90° C. and refluxed for 45 min. After cooling to room temperature, saturated Na$_2$CO$_3$ was added until the pH was neutral by pH paper. 50 mL of ethyl acetate was then added. The organic layer was washed with water (25 mL), Brine (25 ml), dried over Na$_2$SO$_4$ and concentrated to give the crude hydroxychromone products (10,22) which were purified by the appropriate measure to give the desired product at fair to excellent yield (20-90%).

5-Hydroxy-2-(2-phenylethyl)chromone (10). Purified by column chromatography by gradient elution from 50:50 dichloromethane/hexane to 100% dichloromethane. IR (diamond cm$^{-1}$) 2934, 1653, 1616, 1480, 1409, 1258, 845, 802; $^1$H NMR (400 MHz, CDCl$_3$): δ 12.51 (1H, s, 5-OH), 7.44 (1H, t, J=8.32 Hz), 7.18-7.32 (5H, m), 6.85 (1H, dd, J=8.4 and 0.8 Hz), 6.76 (1H, dd, 0.1=8.4 and 0.8 Hz), 6.06 (1H, s), 3.05 (2H, t, J=7.0 Hz), 2.92 (2H, t, J=6.8 Hz); $^{13}$C NMR (100 MHz, CDCl$_3$) δ 183.5, 169.8, 160.8, 156.7, 139.4, 135.1, 128.7, 128.2, 126.6, 111.2, 110.6, 108.8, 106.6, 36.0, 32.8; HREIMS (positive) m/z 265.10 [M$^+$] (calcd for C$_{17}$H$_{14}$O$_3$, 265.10).

5-Hydroxy-2-(phenoxymethyl)chromone (22a). Purified by column chromatography eluting with 3:1 dichloromethane:hexanes and precipitation from acetone. IR (diamond cm$^{-1}$) 3082, 2903, 1655, 1628, 1497, 1431, 1384, 1240, 863, 803; $^1$H-NMR (400 MHz, DMSO-d$_6$): δ, 12.47 (1H, s), 7.67 (1H, t J=8.36 Hz), 7.34 (2H, dt, J=2.04 and 8.72 Hz), 7.11-6.99 (4H, m), 6.84 (1H, dd 3=7.6 and 8.24 Hz) 6.54 (1H, s), 5.17 (2H, s); $^{13}$C-NMR (100 MHz, DMSO-d$_6$) δ 182.8, 166.1, 159.9, 157.3. 156.0, 136.1, 129.6, 121.6, 114.8, 111.1, 110.1, 108.1, 107.3, 65.3; HREIMS (positive) m/z 267.10 [M$^+$] (calcd for C$_{16}$H$_{12}$O$_4$, 267.01).

5-Hydroxy-2-(2'-hydroxy-2-phenylethyl)chromone (22b). Purification was done by stirring the crude solid in minimal dichloromethane and collecting the undissolved solid. IR (diamond cm$^{-1}$) 3153, 2944, 1650, 1618, 1583, 1487, 1259, 845, 801; $^1$H NMR (400 MHz, DMSO-d$_6$): δ 12.63 (1H, br. s, 5-OH), 9.48 (1H, br s, 2'-OH), 7.62 (1H, t, J=8.32 Hz), 7.08-6.99 (3H, m), 6.78 (2H, d, J=8.4 Hz), 6.69 (1H, t, J=7.4 Hz) 6.23 (1H, s), 2.95 (4H, s,); $^{13}$C NMR (100 MHz, DMSO-d$_6$) δ 182.9, 171.4, 159.9, 156.2, 155.2, 135.6, 129.8, 127.4, 125.8, 118.8, 114.9, 110.7, 109.8, 108.1, 107.0, 33.5, 27.0; HREIMS (positive) m/z 281.10 [M$^+$] (calcd for C$_{17}$H$_{14}$O$_4$, 281.10).

5-Hydroxy-2-(3'-hydroxy-2-phenylethyl)chromone (22c). Purification was done by stirring the crude solid in minimal dichloromethane and collecting the undissolved solid. IR (diamond cm$^{-1}$) 3220, 2947, 1654, 1614, 1578, 1565, 1245, 843, 801; $^1$H NMR (400 MHz, Acetone-d$_6$): δ 12.67 (1H, s, 5-OH), 7.61 (1H, t, J=8.32 Hz), 7.09 (1H, t, J=7.4 Hz), 6.98 (1H, dt, J=2.4 and 8.4 Hz), 6.69 (3H, m) 6.65 (1H, dt, J=2.4 and 0.84 Hz), 6.18 (1H, s,), 3.05 (4H, m); $^{13}$C-NMR (100 MHz, DMSO-d$_6$) δ 182.9, 170.9, 159.9, 157.3, 156.2, 141.2, 135.7, 129.2, 118.8, 115.2, 113.2, 110.8, 109.8, 108.4, 107.2, 34.8, 31.8; HREIMS (positive) m/z 282.09 [M$^+$] (calcd for C$_{17}$H$_{14}$O$_4$, 282.09).

5-Hydroxy-2-(4'-hydroxy-2-phenylethyl)chromone (22d). Purification was done by stirring the crude solid in minimal dichloromethane and collecting the undissolved solid. IR (diamond cm$^{-1}$) 3381, 2947, 1650, 1616, 1579, 1569, 1250, 845, 800; $^1$H NMR (400 MHz, DMSO-d$_6$): δ 12.62 (1H, s, 5-OH), 7.64 (1H, t, J=8.32 Hz), 7.03 (3H, d, J=8.44 Hz), 6.78 (1H, d, J=8.2 Hz), 6.65 (2H, d, J=8.44 Hz), 6.27 (1H, s), 2.93 (4H, m); $^{13}$C NMR (100 MHz, DMSO-d$_6$) δ 182.8, 171.1, 159.5, 156.2, 155.4, 135.7, 129.9, 129.2, 115.0, 110.7, 109.7, 108.4, 107.3, 35.5, 31.1; HREIMS (positive) m/z 282.09 [M$^+$] (calcd for C$_{17}$H$_{14}$O$_4$, 282.09).

5-Hydroxy-2-(2-(thiophen-2-yl)ethyl)chromone (22e): Purified by column chromatography eluting with 50/50 hexanes/dichloromethane. IR (diamond cm$^{-1}$) 3103, 3066, 2913, 1645, 1613, 1474, 1439, 1379, 1357, 1239, 840, 807; $^1$H-NMR (400 MHz, Acetone-d$_6$): δ, 12.64 (1H, s), 7.61 (1H, t, J=8.36 Hz), 7.25 (1H, dd, J=2.16 and 4.2), 6.99 (1H, dd, J=0.72 and 8.44 Hz), 6.93-6.91 (2H, m) 6.75 (1H, dd, J=0.6 and 8.28), 6.22 (1H, s) 3.35 (2H, t, J=7.24 Hz), 3.09 (2H, t, J=7.64); $^{13}$C-NMR (100 MHz, Acetone-d$_6$) δ 184.3, 170.9, 161.8, 157.7, 143.1, 136.3, 127.8, 126.0, 124.7 111.7, 111.1, 109.6, 107.8, 36.7, 27.4; HREIMS (positive) m/z 271.04 [M$^+$] (calcd for C$_{15}$H$_{12}$O$_3$S, 271.04).

5-Hydroxy-2-(2-(furan-2-yl)ethyl)chromone (22f). Purification by column chromatography eluting with 80/20 hexanes ethyl acetate. IR (diamond cm$^{-1}$) 3144, 3121, 2917, 1645, 1615, 1593, 1581, 1313, 1295, 1262, 838, 808; $^1$H NMR (400 MHz, Acetone-d$_6$): δ 12.65 (1H, s, 5-OH), 7.61 (1H, t, J=8.32 Hz), 7.43 (1H, d, J=1.68 Hz), 6.96 (1H, d, J=8.4 Hz), 6.74 (1H, d, J=8.24 Hz), 6.31 (1H, dd, 1.92 and 8.4 Hz), 6.23 (1H, s), 6.15 (1H, d, J=3.2 Hz), 3.13 (2H, t, 7.0 Hz), 3.03 (2H, t, 7.0 Hz); $^{13}$C NMR (100 MHz, Acetone-d$_6$) δ 182.3, 171.1, 161.7, 157.7, 154.5, 142.5, 136.3, 111.7, 111.2, 109.3, 107.6, 106.8, −33.4, −25.7.; HREIMS (positive) m/z 255.07 [M$^+$] (calcd for C$_{15}$H$_{12}$O$_4$, 255.07).

5-Hydroxy-2-benzyl chromone (22g): Purified by column chromatography eluting with 80/20 Hexanes/Ethyl Acetate. IR (diamond cm$^{-1}$) 3098, 3055, 2788, 1667, 1618, 1482, 1434, 1372, 1263, 864, 820; $^1$H-NMR (400 MHz, Acetone-d$_6$): δ, 12.62 (1H, s), 7.569 (1H, t, J=8.4 Hz), 7.43-7.28 (5H, m), 6.89 (1H, dd, J=0.68 and 8.48 Hz), 6.72 (1H, dd J=0.52 and 8.24 Hz) 6.16 (1H, s), 4.05 (1H, s); $^{13}$C-NMR (100 MHz, Acetone-d$_6$) δ 184.4, 171.2, 161.8, 157.7, 136.4, 136.2, 130.1, 129.7, 128.2, 111.7, 111.1, 109.6, 107.7, 40.8. HREIMS (positive) m/z 251.07 [M$^+$] (calcd for C$_{16}$H$_{12}$O$_3$, 251.07).

5-Hydroxy-2-(3-phenylpropyl)chromone (22h): Purified by column chromatography eluting with 80/20 Hexanes/Ethyl Acetate. IR (diamond cm$^{-1}$) 3025, 2930, 1652, 1618, 1475, 1459, 1367, 1252, 845, 802; $^1$H-NMR (400 MHz, CDCl$_3$): δ, 12.54 (1H, s), 7.47 (1H, t, J=8.32 Hz), 7.31-7.17 (5H, m), 6.83 (1H, dd, J=0.64 and 8.4 Hz), 6.77 (1H, d, J=8.24 Hz) 6.09 (1H, s), 2.72 (2H, t, J=7.4 Hz), 2.62 (2H, t, J=7.32), 2.07 (2H, p, J=7.72 Hz); $^{13}$C-NMR (100 MHz, CDCl$_3$) δ 184.5, 170.6, 160.8, 156.7, 140.7, 135.0, 128.5, 128.4, 126.2 111.1, 110.6, 108.5, 106.8, 34.9, 33.6, 28.2. HREIMS (positive) m/z 279.10 [M$^+$] (calcd for C$_{18}$H$_{16}$O$_3$, 279.10).

5-Hydroxy-2-(4-phenylbutyl) chromone (22i): Purified by column chromatography eluting with 70/30 Hexanes/Ethyl Acetate. IR (diamond cm$^{-1}$) 3061, 2933, 2852, 1650, 1621, 1478, 1459, 1382, 1366, 1258, 873, 803; $^1$H-NMR (400 MHz, Acetone-d$_6$): δ, 12.70 (1H, s), 7.59 (1H, t, J=8.32 Hz), 7.28-7.14 (5H, m), 6.95 (1H, dd, J=0.68 and 8.4 Hz), 6.74 (1H, d, J=8.28 Hz) 6.20 (1H, s), 2.77-2.67 (4H, m), 1.83-1.74 (4H, m); $^{13}$C-NMR (100 MHz, Acetone-d$_6$) δ 184.5, 172.6, 161.8, 157.7, 143.0, 136.2, 129.2, 129.1, 126.6 111.6, 111.1, 109.0, 107.7, 36.0, 34.5, 31.5, 27.0; HREIMS (positive) m/z 293.12 [M$^+$] (calcd for C$_{19}$H$_{18}$O$_3$, 293.12).

5-hydroxy-2-((benzyloxy)methyl)chromone (22j): Purified by column chromatography eluting with 70/30 Hexanes/Ethyl Acetate. IR (diamond cm$^{-1}$) 3030, 2951, 2871, 1649, 1585, 1480, 1457, 1420, 1255, 1220, 853, 802; $^1$H-NMR (400 MHz, Acetone-d$_6$): δ, 12.60 (1H, s), 7.57 (1H, t, J=8.32 Hz), 7.43-7.28 (5H, m), 6.90 (1H, dd, J=0.52 and 8.4 Hz), 6.73 (1H, d, J=8.28 Hz), 6.34 (1H, s), 4.71 (2H, s), 4.52 (2H, s); $^{13}$C-NMR (100 MHz, Acetone-d$_6$) δ 184.2, 168.5, 161.8, 157.4, 138.6, 136.5, 129.6, 129.3, 128.9, 128.7, 111.9, 111.7, 111.5, 108.5, 107.9, 73.8, 38.7; HREIMS (positive) m/z 281.08 [M$^+$] (calcd for C$_{17}$H$_{14}$O$_4$, 281.08).

7-Hydroxy-2-(2-phenylethyl)chromone (22k). Purified by column chromatography by elution with 95:5 dichloromethane/MeOH. IR (diamond cm$^{-1}$) 3026, 1621, 1548, 1495, 1421, 1256, 852, 823; $^1$H-NMR (400 MHz, Acetone-d$_6$): δ 9.45 (1H, s, 7-OH), 7.96-7.90 (1H, m), 7.28-7.18 (5H, m), 6.94 (1H, d, J=8.68 Hz), 6.87 (1H, s), 6.00 (1H, s), 3.08 (2H, t, J=7.76 Hz), 2.95 (2H, t, J=6.08 Hz); $^{13}$C NMR (100 MHz, acetone-d$_6$) δ 177.2, 168.7, 163.1, 159.1, 141.2, 129.29, 129.26, 127.7, 127.1, 117.8, 115.2, 110.3, 103.3, 36.2, 33.4.; HREIMS (positive) m/z 265.09 [M$^+$] (calcd for C$_{17}$H$_{14}$O$_3$, 265.09).

7-Hydroxy-2-(2'-hydroxy-2-phenylethyl)chromone (22l): Purified by stirring crude solid in acetone for 24 hrs and then filtering the precipitate. IR (diamond cm$^{-1}$) 3176, 2945, 1626, 1546, 1443, 1227, 842, 818; $^1$H-NMR (400 MHz, DMSO-d$_6$): δ, 10.69 (1H, s), 9.38 (1H, s), 7.94 (1H, d, J=8.72 Hz), 7.06 (1H, dd, J=7.44 and 1.44 Hz), 6.99 (1H, dt, J=1.64 and 7.9 Hz), 6.86 (1H, dd, J=8.7 and 2.2 Hz) 6.79-6.78 (2H, m), 6.68 (1H, t, J=7.4 Hz), 2.90 (4H, m); $^{13}$C NMR (100 MHz, DMSO-$_{d6}$) δ 176.4, 168.6, 162.3, 157.7, 154.9, 129.8, 127.3, 126.5, 125.9, 118.9, 115.8, 114.8, 114.7, 108.9, 102.1, 33.3, 27.0; HREIMS (positive) m/z 282.05 [M$^+$] (calcd for C$_{17}$H$_{14}$O$_4$, 282.09).

7-Hydroxy-2-(3'-hydroxy-2-phenylethyl)chromone (22m): Purified by stirring crude solid in DCM and collecting the ppt. IR (diamond cm$^{-1}$) 3145, 2926, 1626, 1590, 1558, 1402, 1250, 1225, 856, 834; $^1$H-NMR (400 MHz, Acetone-d$_6$): δ, 9.89 (1H, br s), 8.56 (1H, br s), 7.91 (1H, d, J=8.68 Hz), 7.09 (1H, t, J=7.8 Hz), 6.93 (1H, dd, J=8.72 and 2.28 Hz), 6.87 (1H, d, J=2.24 Hz), 6.68 (2H, m), 6.66 (1H, m), 6.0 (1H, s), 3.00 (4H, m); $^{13}$C-NMR (100 MHz, Acetone-d$_6$) δ 177.2, 168.7, 163.1, 159.1, 158.4, 142.8, 130.3, 127.7, 120.4, 117.9, 116.2, 115.2, 114.1, 110.4, 103.3, 36.2, 33.4; HREIMS (positive) m/z 282.09 [M$^+$] (calcd for C$_{17}$H$_{14}$O$_4$, 282.09).

7-Hydroxy-2-(4'-hydroxy-2-phenylethyl)chromone (22n): Purified by column chromatography eluting with 70/30 Hexanes/Ethyl Acetate. IR (diamond cm$^{-1}$) 3181, 2942, 1622, 1596, 1547, 1256, 848, 808; $^1$H-NMR (400 MHz, Acetone-d$_6$): δ, 9.49 (1H, s), 8.11 (1H, s), 7.92 (1H, d, J=8.68 Hz), 7.11 (2H, d, J=8.48 Hz), 6.94 (1H, dd, J=8.7 and 2.24 Hz) 6.89 (1H, d, J=2.24 Hz), 6.77 (2H, d, J=8.48 Hz), 5.99 (1H, m), 3.01 (2H, t, J=8.36 Hz), 2.89 (2H, t, J=8.4 Hz); $^{13}$C-NMR (100 MHz, Acetone-d$_6$) δ 177.1, 168.8, 159.1, 131.9, 130.2, 127.7, 117.9, 116.0, 115.1, 110.4, 103.2, 36.7, 32.7; HREIMS (positive) m/z 305.08 [M$^+$Na] (calcd for NaC$_{17}$H$_{14}$O$_4$, 305.07).

5-hydroxy-2-((naphthalen-2-yloxy)methyl)chromone (22o): Purification was done by stirring the crude solid in minimal acetone and collecting the undissolved solid. IR (diamond cm$^{-1}$) 3057, 1653, 1624, 1474, 1429, 1380, 1235, 866, 801; $^1$H NMR (400 MHz, DMSO-d$_6$): δ 12.47 (1H, s, 5-OH), 7.91-7.82 (3H, m), 7.69 (1H, t, J=8.36 Hz), 7.53-7.47 (2H, m), 7.41-7.32 (2H, m) 7.12 (1H, d, J=8.48 Hz), 6.61 (1H, d, J=8.20 Hz), 6.61 (1H, s), 5.30 (2H, s,); $^{13}$C NMR (100 MHz, DMSO-d$_6$) δ 182.9, 165.9, 159.9, 156.1, 155.2, 136.2, 134.0, 129.6, 128.9, 127.5, 126.8, 126.6, 125.1, 118.3, 111.2, 110.2, 108.2, 107.8, 107.4, 65.5; HREIMS (positive) m/z 318.0828 [M$^+$] (calcd for C$_{20}$H$_{14}$O$_4$, 318.0819).

5-hydroxy-2-((naphthalen-1-yloxy)methyl)chromone (22p): Purification was done by stirring the crude solid in minimal acetone and collecting the undissolved solid. IR (diamond cm$^{-1}$) 3063, 1652, 1624, 1476, 1429, 1377, 1244, 875, 801; $^1$H NMR (400 MHz, DMSO-d$_6$): δ 12.48 (1H, s, 5-OH), 8.28-8.26 (1H, M), 7.93-7.90 (1H, m), 7.69 (1H, t, J=8.36 Hz), 7.58-7.56 (3H, m), 7.45 (1H, t, J=7.94 Hz), 7.16 (1H, d, J=7.52 Hz), 7.09 (1H, t, J=8.36 Hz), 6.85 (1H, d, J=7.98 Hz), 6.65 (1H, s), 5.38 (2H, s); $^{13}$C-NMR (100 MHz, DMSO-d$_6$) δ 182.9, 166.1, 159.9, 156.1, 152.7, 136.2, 134.1, 127.5, 126.7, 125.9, 125.8, 124.8, 121.4, 111.2, 110.2, 108.0, 107.4, 106.3, 65.9; HREIMS (positive) m/z 318.0828 [M$^+$] (calcd for C$_{20}$H$_{14}$O$_4$, 318.0819).

5-hydroxy-2-(naphthalen-1-ylmethyl)chromone (22q). Purified by column chromatography by gradient elution from 50:50 dichloromethane/hexane to 100% dichloromethane. IR (diamond cm$^{-1}$) 3059, 1650, 1617, 1475, 1435, 1358, 1257, 865, 800; $^1$H NMR (400 MHz, Acetone-d$_6$): δ 12.57 (1H, s, 5-OH), 8.17 (1H, d, J=8.24 Hz), 7.95 (1H, d, J=7.6 Hz), 7.93 (1H, d, J=8.16 Hz), 7.61-7.50 6.76 (5H, m), 6.89 (1H, d, J=7.8 Hz), 6.71 (1H, d, J=8.3 Hz), 6.05 (1H, s), 4.55 (2H, s); $^{13}$C NMR (100 MHz, Acetone-d$_6$) δ 184.2, 171.2, 161.8, 157.7, 136.4, 135.0, 132.9, 132.0, 129.7, 129.2, 129.1, 127.4, 126.9, 124.7, 111.8, 111.1, 109.8, 107.8, 37.9; HREIMS (positive) m/z 302.0883 [M$^+$] (calcd for C$_{20}$H$_{14}$O$_3$, 302.0870).

5-hydroxy-2-(thiophen-2-ylmethyl)chromone (22r): Purified by Column chromatography eluting with 70/30 Hexanes/Ethyl Acetate. IR (diamond cm$^{-1}$) 3061, 2933, 2852, 1650, 1621, 1478, 1459, 1382, 1366, 1258, 873, 803; $^1$H-NMR (400 MHz, Acetone-d$_6$): δ, 12.58 (1H, s), 7.60 (1H, t, J=8.36 Hz), 7.39 (1H, dd J=1.16 and 5.12 Hz), 7.12 (1H, dd, J=0.88 and 3.4 Hz), 7.03 (1H, dd, J=3.48 and 5.12 Hz) 6.96 (1H, dd J=0.68 and 8.44 Hz), 6.74 (1H, dd, J=0.52 and 8.24 Hz), 6.24 (1H, s) 4.29 (1H, s); $^{13}$C-NMR (100 MHz, Acetone-d$_6$) δ 184.4, 170.1, 161.8, 157.6, 137.3, 136.5, 128.3, 128.1, 126.4 111.8, 111.1, 109.3, 107.8, 34.8; HREIMS (positive) m/z 257.0273 [M$^+$] (calcd for C$_{14}$H$_{10}$O$_3$S, 257.0278).

5-hydroxy-2-(phenethoxymethyl)chromone (22s): Purified by column chromatography eluting with 50:50 dichloromethane:hexanes. IR (diamond cm$^{-1}$) 3069, 2935, 2858, 1650, 1599, 1497, 1429, 1397, 1246, 870, 804; $^1$H-NMR (400 MHz, Acetone-d$_6$): δ, 12.59 (1H, s, 5-OH), 7.58 (1H, t J=8.34 Hz), 7.29-7.25 (4H, m), 7.21-7.17 (1H, m), 6.89

(1H, d, J=8.44 Hz), 6.73 (1H, d, J=8.26 Hz), 6.27 (1H, s), 4.48 (2H, s), 3.85 (2H, t, J=6.82 Hz), 2.95 (2H, t, J=6.82 Hz); $^{13}$C-NMR (100 MHz, Acetone-d$_6$) δ 184.2, 168.8, 161.8, 157.4. 139.8, 136.5, 129.8, 129.2, 127.1, 111.8, 111.5, 108.2, 107.9, 107.8, 73.1, 69.2, 36.8; HREIMS (positive) m/z 296.0977 [M$^+$] (calcd for C$_{18}$H$_{16}$O$_4$, 296.0976).

Pharmacology:

% Inhibition studies, K$_i$ determinations, receptor binding profiles, agonist and/or antagonist functional data was generously provided by the National Institute of Mental Health's Psychoactive Drug Screening Program, Contract # HHSN-271-2008-00025-C (NIMH PDSP).

Molecular Modeling Studies:

The chemical structures of the two ligands 5-HPEC and 5-HPPC were sketched within SYBYL-X2.0, and their Gasteiger-Hückel charges were assigned before energy minimization (10,000 iterations) under the TAFF. The genetic algorithm docking program GOLD[54] was used to perform the docking studies with standard default settings unless otherwise specified. The binding site was defined to include all atoms within 10 Å of the α-carbon atom of Asp135 for 5-HT$_{2B}$ crystal structure (PDB ID-4IB4[48]). The obtained GOLD-docked solutions were merged into the receptor and the combined receptorligand structures were energy-minimized using the parameters described above in order to remove clashes and minimize strain energy, thus optimizing the interactions between ligand and receptor within the binding pocket. These models were then subjected to hydropathic analysis with the HINT[49] program, and best-scored HINT solutions were obtained. The pictures shown herein were generated using the PyMOL Molecular Graphics System, Version 1.5.0.4 Schrödinger, LLC.

Results

Chemistry.

Figure 13:
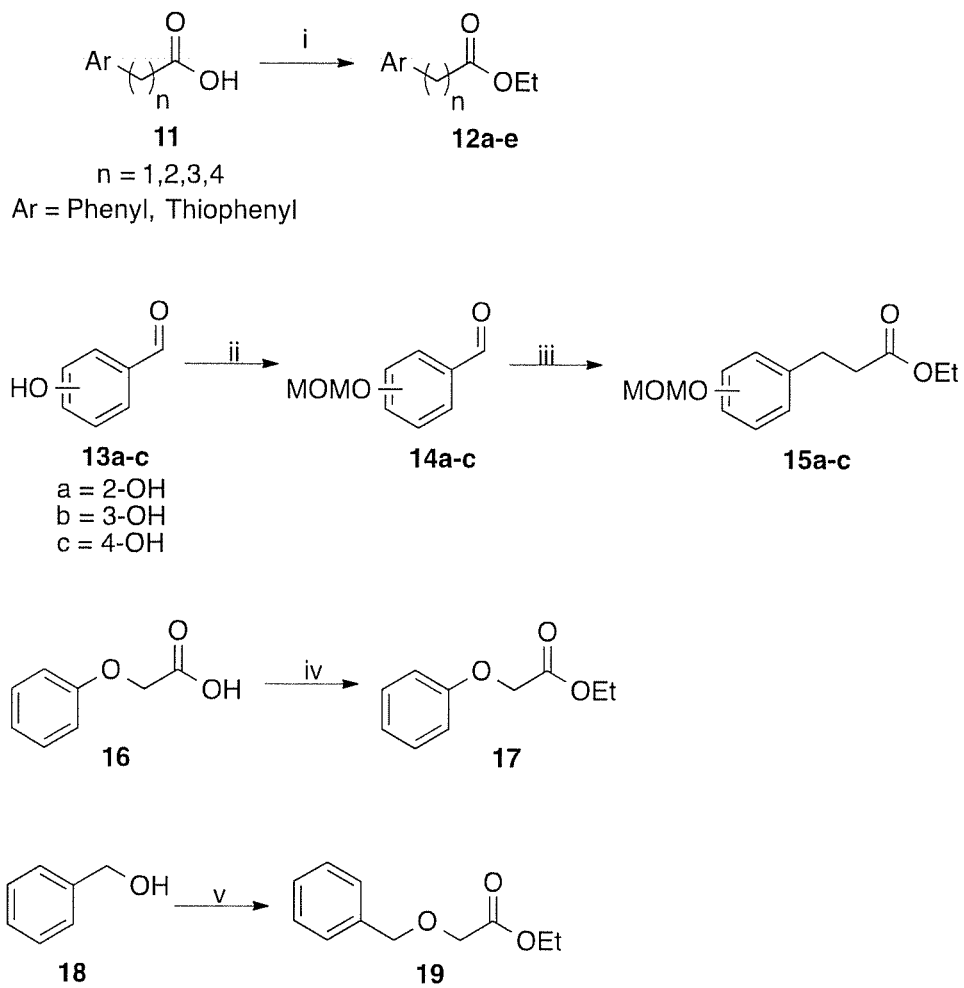
FIG. 13. Synthesis of esters for Claisen condensation Reagents and Conditions: (i) H$_2$SO$_4$ (cat.) EtOH, reflux 24 hrs; (ii) DCM, DIPEA, MOMCl, rt, 3 hrs; (iii) 1. DBU, triethyl phosphonoacetate, rt, 4 hrs 2. H$_2$, Pd/C (10 mol %), 60 atm, 2 hrs. (iv) 1.CDI, THF, rt, 30 min, 2. EtOH, rt, 16 hrs; (v) 1. NaH, THF, 0° C. 1 hr 2. Ethyl-2-bromoacetate, 0° C., 16 hrs.

To explore the potential structural requirements for 5-HT$_{2B}$ binding, a series of natural and non-natural 2-(2-phenylethyl)chromones (22a-n, Table 6) were synthesized. For each derivative the chromone core remains constant with diversity being introduced primarily at the C2, C7 and the "C" ring. The first step was the synthesis of the needed esters (12a-e, 15a-c, 17 and 19, FIG. 13). Several methodologies were employed depending upon the available starting materials. The synthesis of ethyl 2-phenylacetate (12a), ethyl 3-phenylpropanoate (12b), ethyl 4-phenylbutanoate (12c), ethyl 5-phenylpentanoate (12d) and ethyl 3-(thiophen-2-yl)propanoate (12e) was accomplished via Fischer esterification.[55] Refluxing the appropriate carboxylic acid in ethanol with catalytic sulfuric acid produced the desired ester in quantitative yield which after work up was used without further purification. The synthesis of the esters used to examine the substitution pattern of the "C" ring was carried out in three steps. First the hydroxyl group of 13 was protected with MOM by reaction with MOMCl in DCM.[38] The protected aldehyde (14) was then reacted in a modified Horner-Wadsorth Emmons reaction with triethyl phosphonoacetate to yield the α,β-unsaturated ester which was reduced in quantitative yield to afford the substituted alkanes 15a-c.[56] Ethyl 2-phenoxyacetate (17) was synthesized by activation of phenoxyacetic acid (16) with CDI followed by the addition of absolute ethanol.[57] The final ester synthesized was ethyl 2-(benzyloxy)acetate (19). Benzyl alcohol was first reacted with sodium hydride at 0° C. and then ethyl-2-bromoacetate was added to give the desired ester 19.

TABLE 6

% Inhibition of radioligand binding at 5-HT$_2$ receptors by (10, 22a-s) at 10 μM. Inhibition ≥50% is deemed significant.

| | R$_1$ | R$_2$ | R$_3$ | 5-HT$_{2A}$ | 5-HT$_{2B}$ | 5-HT$_{2C}$ |
|---|---|---|---|---|---|---|
| 10 | OH | H | phenethyl | 14.2 | 62.6 | 4.8 |
| 22a | OH | H | phenoxymethyl-CH$_2$ | 0.2 | 50.0 | 7.0 |
| 22b | OH | H | 2-hydroxyphenethyl | 24.3 | 12.8 | 23.8 |
| 22c | OH | H | 3-hydroxyphenethyl | 39.0 | 76.3 | 30.4 |

TABLE 6-continued
% Inhibition of radioligand binding at 5-HT$_2$ receptors by (10, 22a-s) at 10 μM.
Inhibition ≥50% is deemed significant.
| | R$_1$ | R$_2$ | R$_3$ | 5-HT$_{2A}$ | 5-HT$_{2B}$ | 5-HT$_{2C}$ |
|---|---|---|---|---|---|---|
| 22d | OH | H | 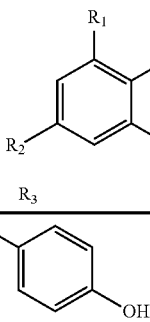 | 12.1 | 70.9 | 56.6 |
| 22e | OH | H | 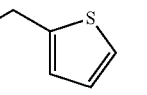 | 1.4 | 74.8 | 19.6 |
| 22f | OH | H | 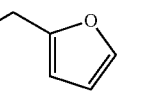 | 12.4 | 68.8 | 24.2 |
| 22g | OH | H | 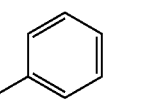 | 1.4 | 30.6 | 24.8 |
| 22h | OH | H | 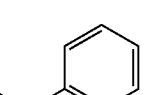 | 5.4 | 70.4 | 7.9 |
| 22i | OH | H | 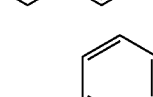 | 5.7 | 45.2 | 14.7 |
| 22j | OH | H | 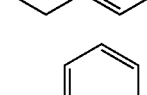 | 3.2 | 77.7 | 42.1 |
| 22k | H | OH | 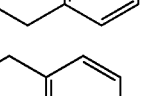 | 35.5 | 34.2 | 33.7 |
| 22l | H | OH | 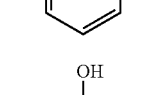 | 47.9 | 16.6 | 44.0 |
| 22m | H | OH | 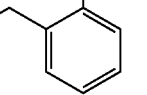 | 23.2 | 25.3 | 0.0 |
| 22n | H | OH | 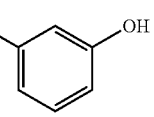 | 33.3 | 40.8 | 53.1 |
| 22o | OH | H | 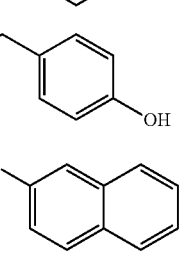 | −3.0 | 2.9 | −0.7 |

TABLE 6-continued

% Inhibition of radioligand binding at 5-HT$_2$ receptors by (10, 22a-s) at 10 μM.
Inhibition ≥50% is deemed significant.

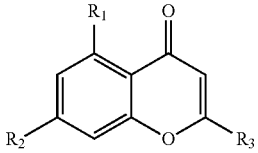

| | R$_1$ | R$_2$ | R$_3$ | 5-HT$_{2A}$ | 5-HT$_{2B}$ | 5-HT$_{2C}$ |
|---|---|---|---|---|---|---|
| 22p | OH | H | 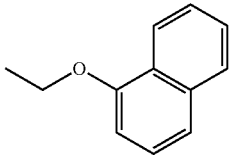 | −1.1 | 11.8 | 0.7 |
| 22q | OH | H | 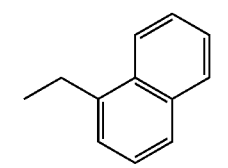 | 9.5 | 17.4 | 2.1 |
| 22r | OH | H | 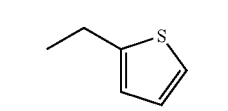 | −4.5 | 31.5 | 23.5 |
| 22s | OH | H | 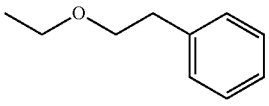 | 0.3 | 77.7 | 11.7 |

Figure 14:
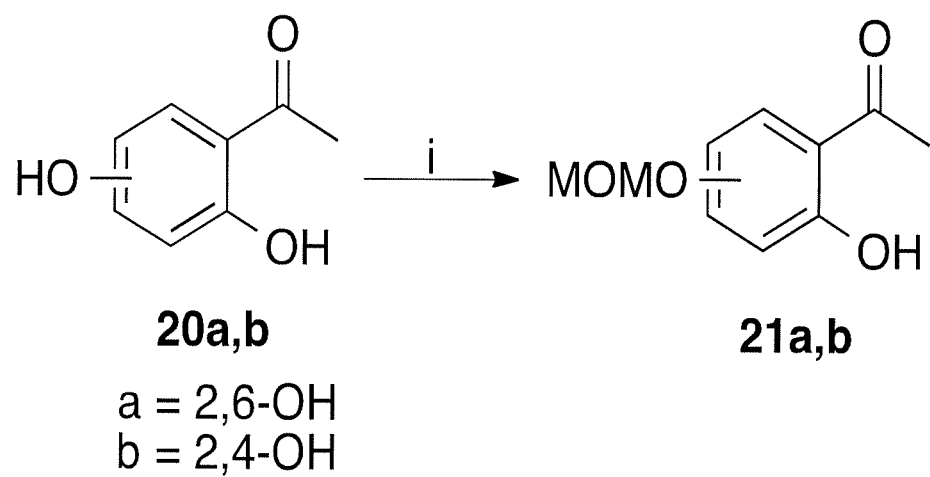
FIG. 14. Protection of dihydroxyl acetophenone derivatives for Claisen Condensation. (i) DCM, DIPEA, MOMCl, rt, 1 hr.
Figure 15:
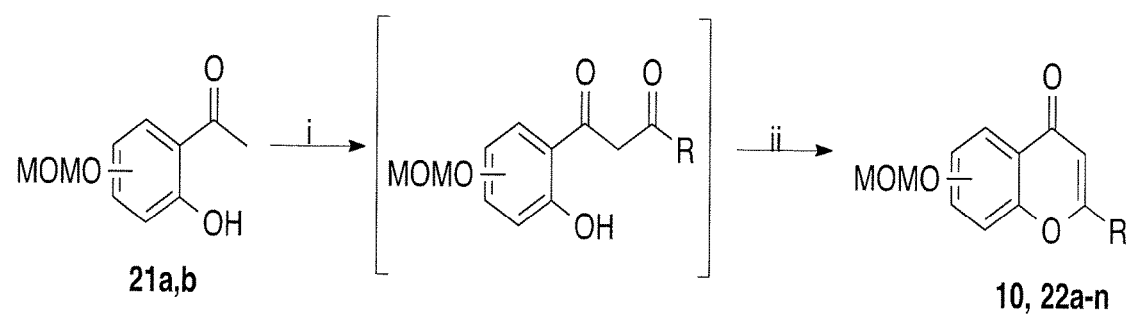
FIG. 15. Synthesis of 2-(2-phenylethyl)chromone derivatives via a Claisen Condensation cyclization approach. Reagents and Conditions: (i) 1. NaH, THF, reflux 1 hr 2. Ester, THF, reflux, 4 hrs; (ii) MeOH, HCl (12 drops), reflux, 45 min.

In the initial synthesis of 5-HPEC, it was determined that monoprotection of the starting dihydroxyacetopheone (20a) was required (Example 1).[22] Accordingly, the same strategy was employed in the synthesis of the proposed analogues. Acetophenones 20a, b were first protected as previously described (FIG. 14).[38] The protected acetophenone (21a, b) was then refluxed with sodium hydride to generate the needed enolate. Following enolate formation, the desired ester (12, 15, 17 or 19) was added and the mixture was refluxed further for 4 hours. Upon work-up, the crude condensation product was then used directly for the cyclization without purification (FIG. 15). Refluxing in methanol with catalytic HCl produced the desired chromone analogues (10, 22a-n). The analogues synthesized are shown in Table 6.[22]

Radioligand Ligand Binding Assays.

Examples 2 and 3 confirmed that 5-HPEC was selective for 5-HT$_{2B}$ over other 5-HT$_2$ receptors. A further objective of the invention was to synthesize analogues of 5-HPEC to improve selectivity and affinity at the 5-HT$_{2B}$ receptor. The screening of these analogues was done in two phases. The initial screening measured the inhibition of radioligand binding (at each of the 5-HT$_2$ receptors) by each new compound (at 10 μM). Those compounds showing greater than 50% inhibition were then further tested for their affinity at the designated receptor. The results of the initial screening are shown in Table 6.

The initial screening of 5-HPEC (10) showed significant inhibitory activity (62%) solely at 5-HT$_{2B}$. We first examined replacement of CT with an oxygen atom to determine the effects of alkyl chain composition on inhibitory activity (22a). This replacement maintains selectivity in the inhibitory assay, showing significant inhibition only at 5-HT$_{2B}$; however, the activity was reduced to 50%. This could suggest a possible hydrophobic requirement within the binding pocket. We next sought to investigate the effects of "C" ring substitutions on inhibitory activity. Along with 5-HPEC the natural product, 5-hydroxy-2-(2'-hydroxy-2-phenylethyl)chromone (22b) was also isolated. Addition of the hydroxyl group at C2' significantly reduces inhibitory activity at 5-HT$_{2B}$. The un-natural analogue 22c in which the hydroxyl group is in the C3' position showed increased inhibitory activity at 5-HT$_{2B}$ to 76% and maintained selectivity. Substitution at C4' with a hydroxyl group (22d), maintains significant inhibitory activity at 5-HT$_{2B}$ (71%) however the selectivity was lost and significant inhibitory activity at 5-HT$_{2C}$ was increased to 56.6%. This observation demonstrates that the C4' position is important for 5-HT$_{2B}$, 5-HT$_{2C}$ selectivity. We next explored the nature of the aromatic "C" ring on inhibitory activity at 5-HT$_{2B}$ by changing the aromatic moiety from a phenyl ring to a thiophene (22e) or furan (22f). These changes maintained significant inhibitory activity and selectivity for the 5-HT$_{2B}$ receptor.

In addition to the above structural changes, the length of the C2 alkyl chain was also modified. Decreasing C2 alkyl chain length to give 2-benzyl-5-hydroxy-chromone (22g) decreases inhibitory activity at the targeted receptor. Conversely, when the alkyl spacer was extended to give 5-hydroxy-2-(3-phenylpropyl)chromone (5-HPPC, 22h) inhibitory activity at 5-HT$_{2B}$ was improved over that of 5-HPEC without a negative impact on selectivity. However, further extension of the alkyl chain to give 5-hydroxy-2-(4-phenylbutyl)chromone (22i) decreases inhibitory activity at the targeted receptor. Given the widespread availability of benzyl alcohols and the improved inhibitory activity of 5-HPPC 22h over 5-HPEC, 2-((benzyloxy)methyl)-5-hydroxychromone 22j was also synthesized in which C8' was replaced with an oxygen atom. Unlike 22a this change led to an increase in inhibitory activity (78%) which was comparable to that of 22h. Though not raised to significant levels, this change did lead to an increase in inhibitory activity at 5-$HT_{2C}$, suggesting a possible loss in selectivity.

The activity of other 2-(2-phenylethyl)chromones archetypes at 5-$HT_{2B}$ was also examined. Although the naturally occurring 7-hydroxy-2-(2-phenylethyl)chromone (22k, 7-HPEC) had been isolated, no biological activity for it has been reported. In the initial isolation of 5-HPEC by Yoon, it was noted that removal of the C5 hydroxyl dramatically reduces neuroprotective activity.[17] Therefore this study sought to examine the necessity of the C5-hydroxy substituent on inhibitory activity at 5-$HT_2$ receptors. When the hydroxyl group is moved from C5 to C7 to afford 7-HPEC, the inhibitory activity at 5-$HT_{2B}$ is reduced to non-significant levels, demonstrating that the C5 hydroxyl is important for activity at 5-$HT_{2B}$. Moreover, selectivity appears reduced; as the inhibitory activity of 7-HPEC at all the 5-$HT_2$ receptors are nearly equivalent. Nevertheless, the effect of the substitution pattern on the "C" ring of these 7-HPEC analogues was also investigated. None of these analogues (22l-n) were able to restore significant inhibitory activity at 5-$HT_{2B}$; however 22n which bears the hydroxyl at C4' did show significant inhibitory activity (53%) at 5-$HT_{2C}$. The 5-HPEC analogue 22d which also bears a hydroxyl at C4' also showed increased activity towards 5-$HT_{2C}$. This further demonstrates that the C4' position is critical for 5-$HT2_B$, 5-$HT2_C$ selectivity.

Following the inhibition studies, those analogues showing greater than 50% inhibitory activity were further examined for their binding affinity at the appropriate receptor. These data are shown in Table 7. 5-Hydroxy-2-(phenoxymethyl)chromone (22a) showed 50% inhibition in the primary screening; however, the affinity at 5-$HT_{2B}$ was negligible ($pK_i$<5). 5-hydroxy-2-(3-hydroxyphenethyl)chromone 22c showed an approximate two fold increase in affinity over 5-HPEC ($pK_i$=5.9). 5-hydroxy-2-(4-hydroxyphenethyl)chromone (22d) also shows a two fold increase in affinity at 5-$HT_{2B}$. However, the 5-$HT_{2B}$ selectivity of 22d was decreased as the $pK_i$ at 5-$HT_2$c was determined to be 5.9. These results indicate that substitution on the "C" ring at C3' is tolerated. Replacing the "C" ring with the thiophene (22e) or furan (22f) showed a two fold improvement in affinity over 5-HPEC with $pK_i$ values of 5.9 and 5.7 respectively. The most dramatic improvement in affinity however was seen with 5-hydroxy-2-(3-phenylpropyl)chromone (5-HPPC, 22h) in which 5-$HT_{2B}$ affinity was improved by ten-fold ($pK_i$=6.6). The replacement of the C8' to give the benzyloxy derivative 22j decreases the 5-$HT_{2B}$ affinity 6 fold when compared to that of 5-HPPC (22h). This observation demonstrates that non-nonpolar moieties at the C2 position are preferred. The final analogue examined for affinity at 5-$HT_2$ receptors was 7-hydroxy-2-(4-hydroxyphenethyl)chromone (22n). This analogue shows moderate affinity for 5-$HT_{2C}$ with a $pK_i$=5.6. Again, this observation confirms that the C4' position is critical for selectivity between 5-$HT_{2B}$ and 5-HT %. This observation also highlights the critical role of the C5-OH for affinity at 5-$HT_{2B}$.

TABLE 7

$pK_i$ values for Analogues that showed ≥50% inhibitory activity in the primary assay.

| | Chromone | $pK_i$ at 5-$HT_{2B}$ | $pK_i$ at 5-$HT_{2C}$ |
|---|---|---|---|
| 10 | | 5.61 ± 0.01 | — |
| 22a | | <5.0 | — |
| 22c | | 5.89 ± 0.06 | — |

TABLE 7-continued pK$_i$ values for Analogues that showed ≥50% inhibitory activity in the primary assay.

| Chromone | | pK$_i$ at 5-HT$_{2B}$ | pK$_i$ at 5-HT$_{2C}$ |
|---|---|---|---|
| 22d | [5-hydroxychromone with 2-(4-hydroxyphenyl)ethyl substituent] | 6.00 ± 0.06 | 5.87 ± 0.05 |
| 22e | [5-hydroxychromone with 2-(thiophen-2-yl)ethyl substituent] | 5.98 ± 0.08 | — |
| 22f | [5-hydroxychromone with 2-(furan-2-yl)ethyl substituent] | 5.74 ± 0.05 | — |
| 22h | [5-hydroxychromone with 3-phenylpropyl substituent] | 6.62 ± 0.07 | — |
| 22j | [5-hydroxychromone with benzyloxymethyl substituent] | 5.8 ± 0.05 | — |
| 22n | [7-hydroxychromone with 2-(4-hydroxyphenyl)ethyl substituent] | — | 5.61 ± 0.05 |
| 22s | [5-hydroxychromone with (2-phenylethoxy)methyl substituent] | 5.9 ± 0.05 | — |

It was previously determined in Example 2 that 5-HPEC behaves functionally as an antagonist at 5-HT$_{2B}$.[53] Given the 10 fold increase in affinity of 5-HPPC, it was then determined if it also maintained functional activity as an antagonist at 5-HT$_{2B}$. Calcium mobilization is a critical function of neurons that occurs in response to receptor signaling in vitro and in vivo, and is used in vivo as a surrogate marker of receptor activation. A calcium mobilization assay is recognized by those of skill in the art as a surrogate for receptor activation and initiation of intracellular signaling in vivo, which are critical events that precede the downstream effects on cellular and tissue phenotypes. A calcium mobilization assay in Flp-In HEK cells was performed to investigate the functional activity of 5-HPPC (at 10 uM). Like 5-HPEC, 5-HPPC showed minimal agonist activity (0.23±0.2% of the maximal response) when compared to the endogenous agonist 5-HT. Conversely, when challenged with an $EC_{50}$ dose (1.6 nM) of 5-HT, 5-HPPC demonstrated improved antagonist activity (20.5±0.5% inhibition) when compared to 5-HPEC at 6.9% inhibition. Taken together these results demonstrated that 5-HPPC maintains antagonist activity at the $5-HT_{2B}$ receptor.

Figure 16:
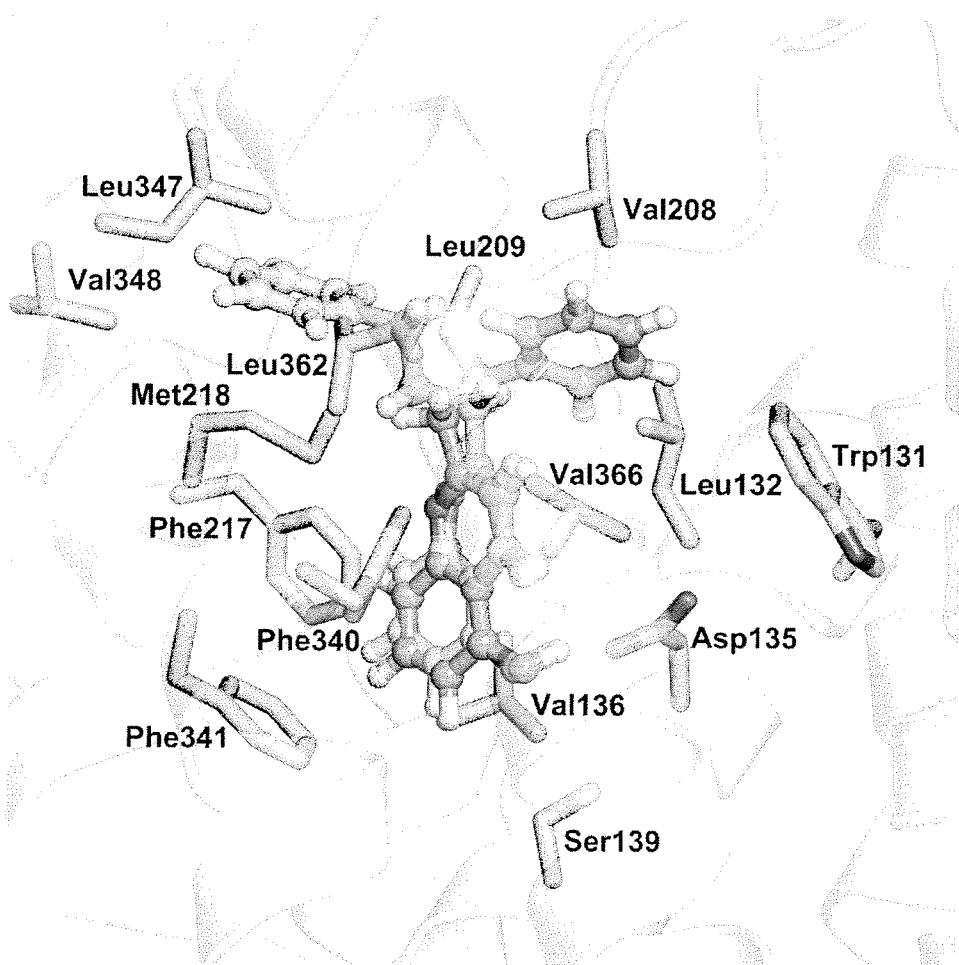
FIG. 16. Ligand binding modes for 5-HPEC and 5-HPPC inside the 5-HT$_{2B}$ receptor. Cartoon representation of the 5-HT$_{2B}$ receptor. Ligands 5-HPEC and 5-HPPC are shown in balls and sticks representation. Amino acid residues involved in interactions are shown in stick representation.

Automated ligand docking experiments on the $5-HT_{2B}$ receptor crystal structure (PDB ID-4IB4) study were undertaken. The docking modes of 5-HPEC and 5-HPPC inside the $5-HT_{2B}$ receptor were similar with the chromone ring occupying an overlapping position. As shown in FIG. 16, the chromone ring was nested inside a hydrophobic pocket walled by Val136, Phe217, Phe340, Phe341 and Val336 residues. Further interactions in this pocket were provided by hydrogen bonding between the Asp135 and the Ser139 residues, and the C5-hydroxyl group of the chromone ring. Compounds 22k-n are unable to participate in the described hydrogen bonding interaction due to their lack of a hydroxyl group at C5 which explains their decreased inhibitory activity at $5-HT_{2B}$. In addition to the importance of the C5 hydroxyl group observed from inhibitory activity data, the affinity data show that the length and composition of the C2 alkyl chain is also important.

As shown in FIG. 16, the C2 alkyl chain of 5-HPEC and 5-HPPC are directed toward the cytoplasmic surface of the receptor. The phenyl ring substituent of 5-HPEC and 5-HPPC can be positioned towards one of two possible hydrophobic pockets. One pocket is formed between helix 5, 6 and 7 (Met218, Leu347, Leu348 and Leu362) and one is formed between extracellular loop 2 and helix 3 (Trp131, Leu132, Val208 and Leu209). Homologation of 5-HPEC to give 5-HPPC extends the nonpolar phenyl ring slightly further into the hydrophobic pocket. This increase in favorable interactions is reflected in an increased HINT score and provides an explanation for the increased affinity of 5-HPPC. Taken together these docking studies are consistent with the observed biological data.

CONCLUSION

Example 4 of the invention demonstrates that 2-(2-phenylethyl)chromone 5-HPEC (10) can serve as a scaffold for the development of non-nitrogenous ligands at the $5-HT_{2B}$ receptor. Such ligands are useful in the study and treatment of diseases and conditions associated with the CNS, including but not limited to Alzheimer's disease, Parkinson's disease, amyotrophic lateral sclerosis, stroke, traumatic brain injury, and drug abuse and addiction, and diseases and conditions associated with the PNS, such as irritable bowel syndrome and pulmonary hypertension. The Examples of the invention identified the structural features of the 2-(2-phenylethyl)chromone scaffold required to maintain and improve affinity and selectivity for $5-HT_{2B}$. Modified natural molecules with hydrocarbon side chains at C2 are preferred, the C5 hydroxyl group is preferred, substitution at C3' is tolerated, and substitution at C4' decreases $5-HT_{2B/C}$ selectivity. Additionally, replacing the "C" phenyl ring with smaller aromatic moieties is also tolerated.

Example 5 provides 5-HPEC analogues and methods for their synthesis. Among the non-natural 5-HPEC analogues, 5-HPPC (22h) showed a ten-fold improvement in affinity at $5-HT_{2B}$ receptors over 5-HPEC. The 5-HPPC analogue also maintained antagonist activity at $5-HT_{2B}$ receptors. A molecular modeling study identified structural features critical for affinity/antagonist activities. These studies identified a primarily hydrophobic binding pocket for the ligands and residues capable of forming hydrogen bonds. Ligand antagonist activity decreased with changes in the position of a hydroxyl group from C5 to C7 on the chromone ring and C2' hydroxyl of the phenyl substituent. This Example demonstrates that the scaffold of the invention can be modified to synthesize novel $5-HT_{2B}$ antagonists for treatments of various diseases and conditions of the CNS and PNS.

REFERENCES

[1] A. S. M. Hung, T. Y. M. Tsui, J. C. Y. Lam, M. S. M. Wai, W. M. Chan, D. T. Yew, *Current Medicinal Chemistry* 2011, 18, 5281-5288.
[2] G. M. Mawe, J. M. Hoffman, *Nature Reviews Gastroenterology & Hepatology* 2013, 10, 473-486.
[3] R. A. Glennon, *Journal of Medicinal Chemistry* 1987, 30, 1-12.
[4] W. E. Childers, A. J. Robichaud, in *Annual Reports in Medicinal Chemistry, Vol 40, Vol.* 40 (Ed.: A. M. Doherty), Elsevier Academic Press Inc, San Diego, 2005, pp. 17-33.
[5] J. E. Leysen, *Current Drug Targets—CNS and Neurological Disorders* 2004, 3, 11-26.
[6] J. Brea, J. Rodrigo, A. Carrieri, F. Sanz, M. I. Cadavid, M. J. Enguix, M. Villazon, G. Mengod, Y. Caro, C. F. Masaguer, E. Ravina, N. B. Centeno, A. Carotti, M. I. Loza, *Journal of Medicinal Chemistry* 2002, 45, 54-71.
[7] J. Brea, J. Castro-Palomino, S. Yeste, E. Cubero, A. Parraga, E. Dominguez, M. I. Loza, *Current Topics in Medicinal Chemistry* 2010, 10, 493-503; G. Poissonnet, J. G. Parmentier, J. A. Boutin, S. Goldstein, *Mini-Reviews in Medicinal Chemistry* 2004, 4, 325-330.
[8] C. Capone, C. Fabrizi, P. Piovesan, M. C. Principato, P. Marzorati, O. Ghirardi, L. Fumagalli, P. Carminati, M. G. De Simoni, *Neuropsychopharmacology* 2007, 32, 1302-1311.
[9] Y. J. Kwon, S. Saubern, J. M. Macdonald, X. P. Huang, V. Setola, B. L. Roth, *Bioorganic & Medicinal Chemistry Letters* 2010, 20, 5488-5490.
[10] B. K. Madras, Z. B. Pristupa, H. B. Niznik, A. Y. Liang, P. Blundell, M. D. Gonzalez, P. C. Meltzer, *Synapse* 1996, 24, 340-348.
[11] M. Goulet, G. M. Miller, J. Bendor, S. H. Liu, P. C. Meltzer, B. K. Madras, *Synapse* 2001, 42, 129-140; B. K. Madras, M. A. Fahey, G. M. Miller, R. De La Garza, M. Goulet, R. D. Spealman, P. C. Meltzer, S. R. George, B. F. O'Dowd, A. A. Bonab, E. Livni, A. J. Fischman, *European Journal of Pharmacology* 2003, 479, 41-51; P. C. Meltzer, A. Y. Liang, P. Blundell, M. D. Gonzalez, Z. M. Chen, C. George, B. K. Madras, *Journal of Medicinal Chemistry* 1997, 40, 2661-2673; P. C. Meltzer, P. Blundell, Y. F. Yong, Z. M. Chen, C. George, M. D. Gonzalez, B. K. Madras, *Journal of Medicinal Chemistry* 2000, 43, 2982-2991.
[12] J. J. La Clair, *Natural Product Reports* 2010, 27, 969-995.
[13] A. M. Edwards, J. B. L. Howell, *Clinical and Experimental Allergy* 2000, 30, 756-774; S. K. Sharma, S. Kumar, K. Chand, A. Kathuria, A. Gupta, R. Jain, *Current Medicinal Chemistry* 2011, 18, 3825-3852.
[14] R. J. Williams, J. P. E. Spencer, C. Rice-Evans, *Free Radical Biology and Medicine* 2004, 36, 838-849.

[15] A. Gomes, M. Freitas, E. Fernandes, J. Lima, *Mini-Reviews in Medicinal Chemistry* 2010, 10, 1-7.
[16] M. K. Kim, H. Yoon, D. L. Barnard, Y. Chong, *Chemical & Pharmaceutical Bulletin* 2013, 61, 486-488.
[17] J. S. Yoon, M. K. Lee, S. H. Sung, Y. C. Kim, *Journal of Natural Products* 2006, 69, 290-291.
[18] K. P. Kwak, *European Neuropsychopharmacology* 2005, 15, S567-S567.
[19] D. Chen, Z. R. Xu, X. Y. Chai, K. W. Zeng, Y. X. Jia, D. Bi, Z. Z. Ma, P. F. Tu, *European Journal of Organic Chemistry* 2012, 5389-5397.
[20] Palop, J. J.; Chin, J.; Mucke, L. *Nature* 2006, 443, 768.
[21] DiNunzio, J. C.; Williams, R. O. *Drug Dev. Ind. Pharm.* 2008, 34, 1141.
[22] Williams, D. A.; Smith, C.; Zhang, Y. *Tetrahedron Lett.* 2013, 54, 4292.
[23] Prisinzano, T. E. *J. Nat. Prod.* 2009, 72, 581.
[24] Katavic, P. L.; Lamb, K.; Navarro, H.; Prisinzano, T. E. *J. Nat. Prod.* 2007, 70, 1278.
[25] Jager, A. K.; Saaby, L. *Molecules* 2011, 16, 1471.
[26] Yang, L.; Qiao, L. R.; Xie, D.; Yuan, Y. H.; Chen, N. H.; Dai, J. G.; Guo, S. X. *Phytochemistry* 2012, 76, 92.
[27] Mattson, M. P. *Neuromol. Med.* 2003, 3, 65.
[28] Wojda, U.; Salinska, E.; Kuznicki, *J. Iubmb Life* 2008, 60, 575.
[29] Wu, B.; Lee, J. G.; Lim, C. J.; Jia, S. D.; Kwon, S. W.; Hwang, G. S.; Park, J. H. *Helv. Chim. Acta* 2012, 95, 636.
[30] Konishi, T.; Konoshima, T.; Shimada, Y.; Kiyosawa, S. *Chem. Pharm. Bull.* 2002, 50, 419.
[31] Li, N. G.; Shi, Z. H.; Tang, Y. P.; Ma, H. Y.; Yang, J. P.; Li, B. Q.; Wang, Z. J.; Song, S. L.; Duan, J. A. *J. Heterocycl. Chem.* 2010, 47, 785.
[32] Alcantara, A. R.; Marinas, J. M.; Sinisterra, J. V. *Tetrahedron Lett.* 1987, 28, 1515.
[33] Smith, J. A.; Maloney, D. J.; Hecht, S. M.; Lannigan, D. A. *Bioorg. Med. Chem.* 2007, 15, 5018.
[34] Zhang, L. P.; Wang, Y. L. *Chem. Res. Chin. Univ.* 2010, 26, 245.
[35] Heilbron, I. M.; Hey, D. H.; Lowe, A. *J. Chem. Soc.* 1934, 1311.
[36] Green, T.; Wuts, P. *Protective Groups in Organic Chemistry*; New Your: John Wiley & Sons, Inc., 1999.
[37] Ghosh, C. K.; Bhattacharyya, S.; Ghosh, C.; Patra, A. *Journal of the Chemical Society-Perkin Transactions 1* 1999, 3005.
[38] Kagawa, H.; Shigematsu, A.; Ohta, S.; Harigaya, Y. *Chem. Pharm. Bull.* 2005, 53, 547.
[39] Nussbaumer, P.; Lehr, P.; Billich, A. *J. Med. Chem.* 2002, 45, 4310.
[40] Nandurkar, N. S.; Bhanushali, M. J.; Patil, D. S.; Bhanage, B. M. *Syn. Commun.* 2007, 37, 4111.
[41] Vauzour, D.; Vafeiadou, K.; Rodriguez-Mateos, A.; Rendeiro, C.; Spencer, J. P. E. *Genes Nutr.* 2008, 3, 115.
[42] Kamei, J.; Igarashi, H.; Kasuya, Y. *Res. Commun Chem. Path.* 1991, 74, 167.
[43] Kamei, J.; Igarashi, H.; Kasuya, Y. *Res. Commun Chem. Path.* 1992, 75, 357.
[44] Madhavan, L.; Freed, W. J.; Anantharam, V.; Kanthasamy, A. G. *J. Pharmacol. Exp. Ther.* 2003, 304, 913.
[45] Kagamiishi, Y.; Shibata, S.; Watanabe, S. *Eur. J. Pharmacol.* 1992, 224, 51.
[46] Fitzgerald, L. W.; Burn, T. C.; Brown, B. S.; Patterson, J. P.; Corjay, M. H.; Valentine, P. A.; Sun, J. H.; Link, J. R.; Abbaszade, I.; Hollis, J. M.; Largent, B. L.; Hartig, P. R.; Hollis, G. F.; Meunier, J. C.; Robichaud, A. J.; Robertson, D. W. *Mol. Pharmacol.* 2000, 57, 75.
[47] Madras, B. K.; Fahey, M. A.; Miller, G. M.; De La Garza, R.; Goulet, M.; Spealman, R. D.; Meltzer, P. C.; George, S. R.; O'Dowd, B. F.; Bonab, A. A.; Livni, E.; Fischman, A. J. *Eur. J. Pharmacol.* 2003, 479, 41.
[48] Wacker, D.; Wang, C.; Katritch, V.; Han, G. W.; Huang, X. P.; Vardy, E.; McCorvy, J. D.; Jiang, Y.; Chu, M. H.; Siu, F. Y.; Liu, W.; Xu, H. E.; Cherezov, V.; Roth, B. L.; Stevens, R. C. *Science* 2013, 340, 615.
[49] Kellogg, G. E.; Abraham, D. J. *Eur. J. Med. Chem.* 2000, 35, 651.
[50] Manivet, P.; Schneider, B.; Smith, J. C.; Choi, D. S.; Maroteaux, L.; Kellermann, O.; Launay, J. M. *J. Bio. Chem.* 2002, 277, 17170.
[51] Knight, A. R.; Misra, A.; Quirk, K.; Benwell, K.; Revell, D.; Kennett, G.; Bickerdike, M. *N-S. Arch. Pharmacol.* 2004, 370, 114.
[52] Rasmussen, S. G. F.; Choi, H. J.; Fung, J. J.; Pardon, E.; Casarosa, P.; Chae, P. S.; DeVree, B. T.; Rosenbaum, D. M.; Thian, F. S.; Kobilka, T. S.; Schnapp, A.; Konetzki, I.; Sunahara, R. K.; Gellman, S. H.; Pautsch, A.; Steyaert, J.; Weis, W. I.; Kobilka, B. K. *Nature* 2011, 469, 175.
[53] D. A. Williams, S. A. Zaidi, Y. Zhang, *Bioorganic & Medicinal Chemistry Letters* 2014, 24, 1489-1492.
[54] M. J. Hartshorn, M. L. Verdonk, G. Chessari, S. C. Brewerton, W. T. M. Mooij, P. N. Mortenson, C. W. Murray, *Journal of Medicinal Chemistry* 2007, 50, 726-741.
[55] E. Fischer, A. Speier, *Chem. Ber.* 1895, 28, 3252-3258.
[56] K. Ando, K. Yamada, *Tetrahedron Letters* 2010, 51, 3297-3299.
[57] H. A. Staab, *Angewandte Chemie International Edition in English* 1962, 1, 351-367.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of inhibiting the serotonin receptor 2B (5-HT$_{2B}$) in a subject, comprising the step of administering to said subject a therapeutically effective amount of at least one compound having the general formula:

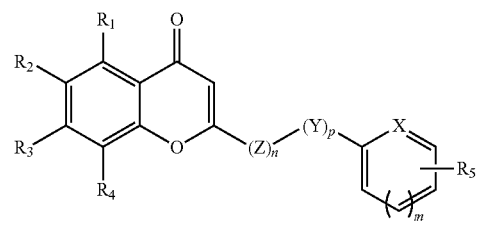

wherein
R1, R2, R3, and R4 can be the same or different and are selected from the group consisting of H, OH, SH, sulfanyl, amino, alkyl, alkoxyl, halogen, alkenyl, alkynyl, aryl, cyano, nitro, carboxyl, carbonyl, sulfone, and sulfoxide;
R5 is either present or absent and if present is selected from the group consisting of OH, SH, sulfanyl, amino, alkyl, alkoxyl, halogen, alkenyl, alkynyl, aryl, cyano, nitro, carboxyl, carbonyl, sulfone, sulfoxide, and a substituted or unsubstituted aromatic or heteroaromatic group connected to any two carbon moieties of the ring structure;

X is S, O, or substituted or unsubstituted $C_1$ alkyl; and

Z and Y can be the same or different and can be present or absent and when present are selected from the group consisting of O and a substituted or unsubstituted $C_1$-$C_4$ alkyl, wherein m, n, and p can be the same or different and are selected from the group consisting of 0, 1, 2, and 3; or salts or solvates thereof, with the proviso that the one or more compounds is not 5-hydroxy-2-phenethyl 4H-chromen-4-one, and wherein said compound is a synthesized non-natural compound.

2. The method of claim 1, wherein said subject has a nervous system disorder.

3. The method of claim 1, wherein said compound is selected from the group consisting of 5-Hydroxy-2-(3'-hydroxy-2-phenylethyl)chromone,
5-Hydroxy-2-(4'-hydroxy-2-phenylethyl)chromone,
5-hydroxy-2-(2-(thiophen-2-yl)ethyl)-4H-chromen-4-one,
5-Hydroxy-2-(2-(furan-2-yl)ethyl)chromone,
5-hydroxy-2-(3-phenylpropyl)-4H-chromen-4-one,
5-hydroxy-2-((benzyloxy)methyl)chromone, and
5-hydroxy-2-(phenethoxymethyl)chromone.

\* \* \* \* \*